United States Patent
Bula et al.

(10) Patent No.: US 12,128,404 B2
(45) Date of Patent: Oct. 29, 2024

(54) MICROFLUIDIC SYSTEM, DEVICE AND METHOD

(71) Applicant: BISU, INC., Wilmington, DE (US)

(72) Inventors: Wojciech Bula, Tokyo (JP); Peter Christian Sommer, Tokyo (JP); Daniel Maggs, Tokyo (JP); Gen Suzuki, Kanagawa (JP)

(73) Assignee: Kohler Ventures, Inc., Kohler, WI (US)

( * ) Notice: Subject to any disclaimer, the term of this patent is extended or adjusted under 35 U.S.C. 154(b) by 0 days.

(21) Appl. No.: 18/231,736

(22) Filed: Aug. 8, 2023

(65) Prior Publication Data

US 2023/0381777 A1 Nov. 30, 2023

Related U.S. Application Data

(63) Continuation of application No. 17/561,754, filed on Dec. 24, 2021, now Pat. No. 11,717,823, which is a continuation of application No. PCT/US2021/041706, filed on Jul. 14, 2021, which is a continuation-in-part of application No. PCT/US2021/012384, filed on Jan. 6, 2021.

(60) Provisional application No. 62/989,895, filed on Mar. 16, 2020, provisional application No. 62/957,536, filed on Jan. 6, 2020.

(51) Int. Cl.
*B01L 3/00* (2006.01)
*B01L 9/00* (2006.01)
*G01N 21/05* (2006.01)

(52) U.S. Cl.
CPC ......... *B01L 3/502715* (2013.01); *B01L 9/527* (2013.01); *G01N 21/05* (2013.01); *B01L 2200/0689* (2013.01); *B01L 2300/0627* (2013.01); *B01L 2300/069* (2013.01); *B01L 2300/0887* (2013.01); *B01L 2300/165* (2013.01)

(58) Field of Classification Search
CPC ....... B01L 3/502715; B01L 2200/0689; B01L 2300/023; B01L 2300/025; B01L 2300/069; B01L 2300/0877; B01L 2300/165; B01L 3/527; B01L 9/527; B01L 2300/0627; G01N 25/60; G01N 2291/02845; G01N 21/03; G01N 21/05; G01N 21/09; G01N 1/10; G01N 2021/0321; G01N 31/22; G01N 31/222
See application file for complete search history.

(56) References Cited

U.S. PATENT DOCUMENTS

2018/0231533 A1* 8/2018 Holmes ............ A61B 5/150969

\* cited by examiner

*Primary Examiner* — Dean Kwak

(57) ABSTRACT

A microfluidic test system is disclosed. The system includes a test substrate including parallel channels and reaction chambers. The reaction chambers are adapted to accommodate optical transmittance, absorbance and reflectance testing. The movement of the fluid within the system is controlled and synchronized in real time with the optical measurements of the reagents and analytes within each individual reaction chamber. The optical testing of each reaction chamber is customized regarding the color and intensity of the source light. The system includes an easy-to-use applicator for the capture of the test fluid and a fully automated measurement and test system. The microfluidic test system may be incorporated into clothing or apparel such as in a diaper. A device and method are also disclosed.

26 Claims, 11 Drawing Sheets

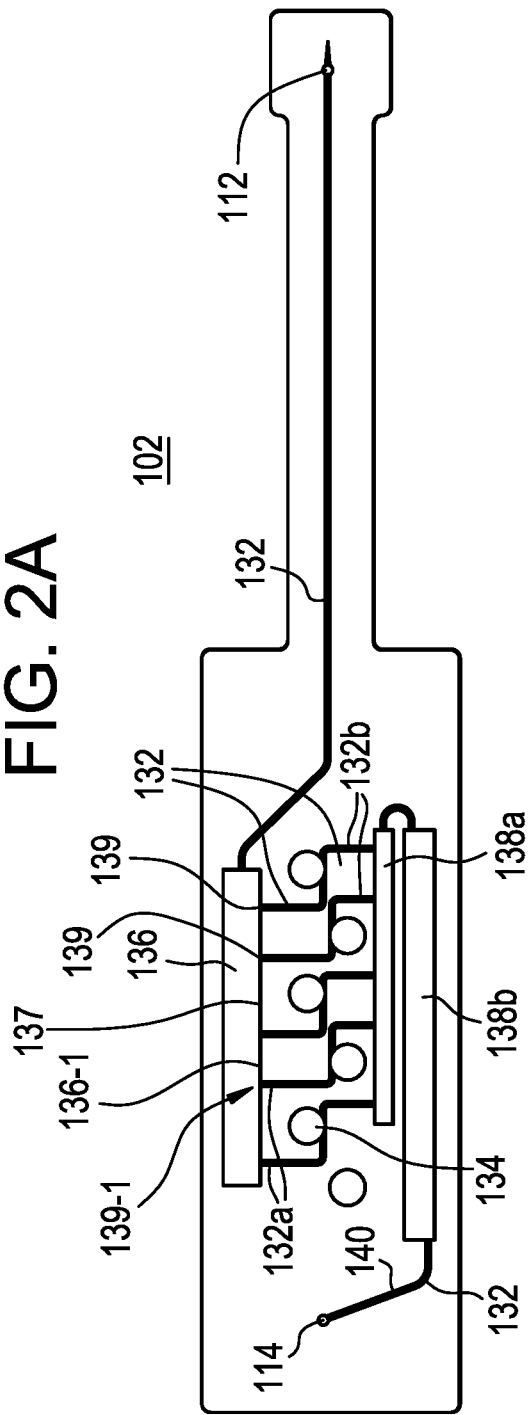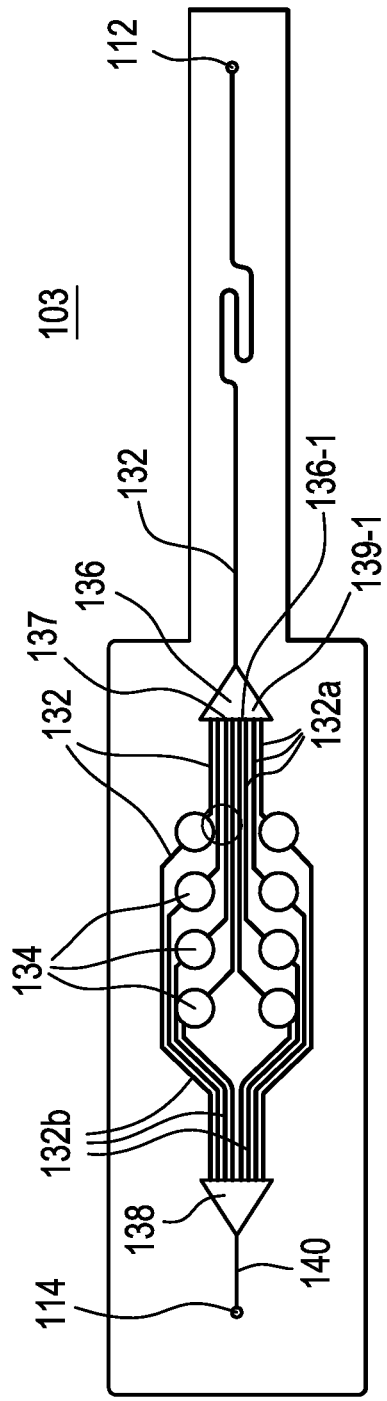

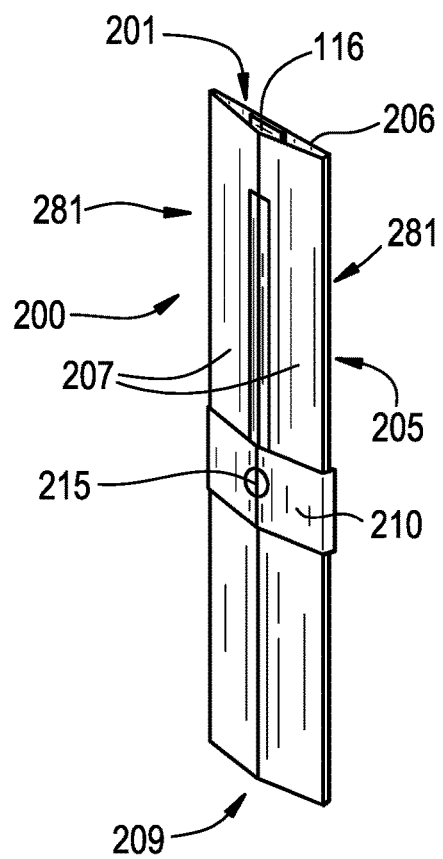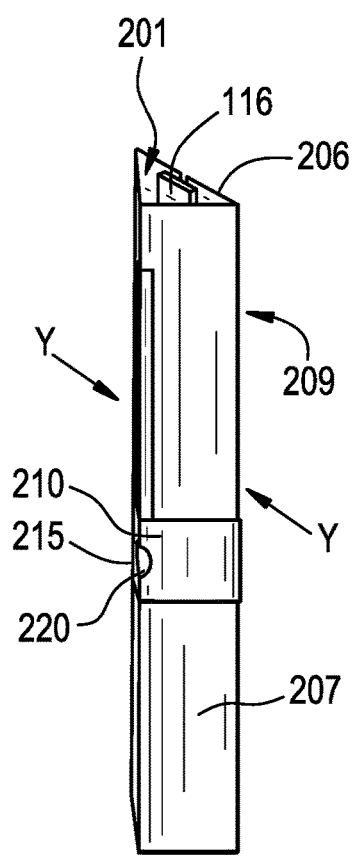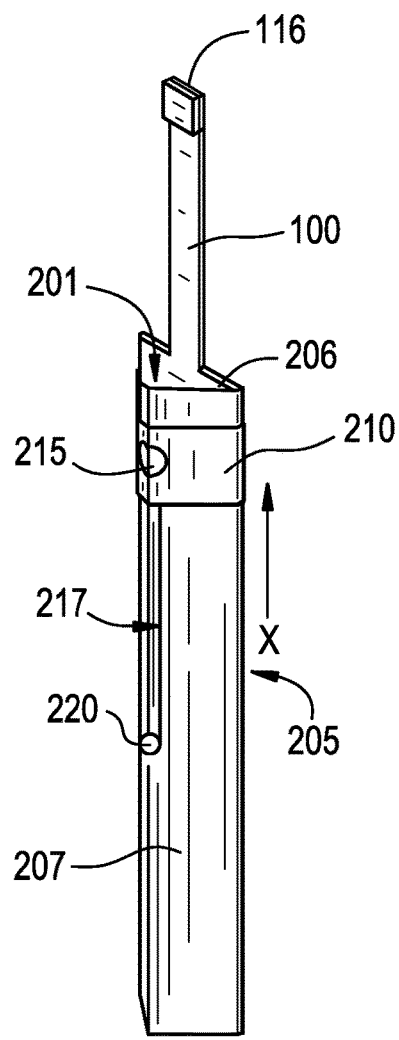

MICROFLUIDIC SYSTEM, DEVICE AND METHOD

FIELD OF THE DISCLOSURE

This disclosure relates to microfluidics, including microfluidic test systems, devices and methods.

BACKGROUND

The following description of the background of the disclosure is provided simply as an aid in understanding and is not admitted to describe or constitute prior art.

Conventional analysis devices for point-of-care diagnostics are devices typically meant to be used by non-technical individuals within a doctor's office or in the field (e.g., at home). Existing point-of-care devices typically require collecting test samples from a patient (e.g., urinating into a cup), distributing the samples onto the test device (e.g., pipetting the sample onto a test strip, or dipping the test strip directly into the sample cup) and then performing the desired measurements (e.g., placing the test strip into a strip reader, or taking a measurement using a smartphone). These devices require the user to collect a significant amount of test sample and carefully perform additional steps to obtain a measurement, a burden which makes the devices inconvenient for high-frequency use at home.

The following references became known from one or more searches conducted in connection with a disclosure of the embodiments described herein. This patent document makes no assertion as to whether or not any particular reference constitutes "prior art" under the patent laws of the various jurisdictions for which patent protection is being sought. Copies are being provided in respective Patent Offices as part of an "Information Disclosure Statement" or equivalent in each jurisdiction.

EP0803288 B1—Higuchi et al., published Mar. 5, 2003
EP1484601 B1—Phelan, published Feb. 4, 2009
U.S. Pat. No. 8,623,635 B2—Nazareth et al., published Jan. 7, 2014
US 2017/0197212 A1—Deshpande, published Jul. 13, 2017
US 2018/0088136 A1—Saji et al., published Mar. 29, 2018
US 2018/0355405 A1—Silveston-Keith et al., published Dec. 13, 2018
US 2019/0302097 A1—Niu et al., published Oct. 3, 2019
Quantifying Colorimetric Assays in Paper-Based Microfluidic Devices by Measuring the Transmission of Light through Paper—Ellerbee et al., published Sep. 1, 2009
Robust dipstick urinalysis using a low-cost, micro-volume slipping manifold and mobile phone platform—Smith et al., published 2016
Lab-on-a-chip based self-monitoring device for dietary intake of potassium and sodium; the LAB-CHIPS study—Vendeville et al., published Sep. 9, 2019 These above-indicated systems, devices and methods are prone to inaccurate readings or other deficiencies.

Accordingly, there is a need for a system or device or method that provides easy-to-use point-of-care diagnostics that performs more accurate types of measurements and is more effective.

SUMMARY OF THE DISCLOSURE

In one aspect, this disclosure provides a microfluidic system comprising a body structure having a first outer layer forming a first side of the body structure; a second outer layer forming a second side of the body structure; a microfluidic assembly including at least a first substrate layer and disposed between the first outer layer and the second outer layer; a first port disposed through the first outer layer and in fluid communication with the microfluidic assembly; and a second port disposed through either the first outer layer or the second outer layer and adapted to be attached to a vacuum source such that a fluid flow path is defined from the first port to the second port through the microfluidic assembly; wherein the microfluidic assembly further includes at least a reaction chamber manifold and a waste reservoir; and two or more fluid flow paths between the reaction chamber manifold and the waste reservoir, wherein each fluid flow path comprises at least one reaction chamber having a dried film, a paper, or a gel including one or more colorimetric test reagents, and wherein the reaction chambers are adapted for an optical measurement of absorbance or transmittance; wherein the reaction chamber manifold has a volume that is greater than, or optionally at least twice the volume of, the volume of a reaction chamber; and wherein the waste reservoir has a volume that is greater than, or optionally at least twice the volume of, the volume of a reaction chamber.

In some embodiments, the body structure comprises a retention reservoir in fluid communication with the first port and adapted to accept an aqueous sample. The retention reservoir may include an absorbent pad may comprise a dried film, a paper, a gel, a sponge, compressed cellulose or any other absorbent material, or any combination thereof.

In some embodiments, any one or more of the reaction chamber manifold, the waste reservoir, or a subsequent reservoir comprise(s) an absorbent material. The absorbent material may comprise a dried film, a paper, a gel, a sponge, compressed cellulose or any other absorbent material, or any combination thereof.

In some embodiments, the second port comprises a hydrophobic or semi-permeable membrane, or both.

In some embodiments, the microfluidic assembly comprises microfluidic channels preferably having a cross-sectional dimension of approximately 0.1-1000 microns inclusive of both limits and all dimensions within the range, and more preferably, at least approximately 0.1, 0.5, 1.0, 5.0, 10, 25, 50, 75, 100, 150, 200, 250, 300, 350, 400, or 450 microns and/or not more than approximately 100, 150, 200, 250, 300, 350, 400, 450, 500, 700, 750, 800, 850 or 1000 microns.

In some embodiments, the system comprises an optical detection system comprising a light source and a detector configured to measure absorbance by or reflectance from at least one of the reaction chambers. The optical detection system may comprise a spectrophotometer or colorimeter comprising a light emitting diode (LED) source and a detector configured to measure transmittance or absorbance through at least one of the reaction chambers, or a smartphone camera sensor or other camera sensor. Further, the reaction chamber(s) optionally abuts the light source/detector to minimize interference from ambient lighting conditions.

In some embodiments, the spectrophotometer comprises a plurality of LED sources and detectors configured to measure transmittance through a plurality of reaction chambers. Optionally, the detectors simultaneously measure transmittance through a plurality of reaction chambers. Optionally, the spectrophotometer is configured such that a single light source and single detector is registered to each of the plurality of reaction chambers.

In some embodiments, the spectrophotometer comprises a single light source, a single detector, and a motor wherein the light source and detector are maintained in a fixed positional relationship and the motor translocates the light source/detector pair sequentially to read a plurality of reaction wells. In some embodiments, the light source/detector pair is held in a fixed position and the motor translocates the microfluidic assembly sequentially to position a plurality of reaction wells within the light source detector assembly for detection and/or quantification.

In other embodiments, the spectrophotometer comprises a single light source, a wave guide configured to split and direct the source light onto a plurality of reaction wells, onto one or more detector(s), or onto a combination thereof, optionally wherein each reaction well is registered to a single detector, or optionally wherein a set of one of more reaction well(s) (or every well) is registered to a discrete set of one or more detector(s). In some such embodiments, additional wave guides may be interposed between the reaction wells and detectors, in order to minimize loss or leakage of light as it passes from each reaction well to a corresponding detector.

In some embodiments, the spectrophotometer comprises multiple light sources configured to direct the source light onto a plurality of reaction wells, a single wave guide or multiple wave guides configured to merge and direct light from a plurality of reaction wells to a single detector or multiple detectors of a number which is less than the number of light sources, wherein each light source is registered to a single reaction well. In some embodiments, the light sources may direct the source light onto a plurality of reaction wells by means of additional wave guides interposed between the light sources and the reaction wells, whereby each light source is connected to each reaction well by means of a wave guide, in order to minimize loss or leakage of light as it passes from the light source to the reaction well.

In some embodiments, at least one detector is configured to measure transmittance or absorbance of at least one wavelength selected from the group consisting of 415 nm, 445 nm, 450 nm, 480 nm, 500 nm, 515 nm, 550 nm, 570 nm, 590 nm, 600 nm, 630 nm, 650 nm, 680 nm and 910 nm, and alternatively or additionally to measure transmittance or absorbance of all discrete wavelengths in the range of 350 nm to 1050 nm or across any other spectrum of a range of wavelengths as a single optical signal integrated over the range of those wavelengths. In some embodiments, one or more of (i) the light source(s) is configured to emit and the detector(s) is configured to detect, light in the infrared, visible, or ultraviolet range.

In some embodiments, the system further comprises a vacuum source adapted to apply a vacuum pressure to the second port.

In some embodiments, the system further comprises a holder having an engagement device, wherein the engagement device is configured to hold the body structure in a retracted position and an extended position, wherein the first port is housed within the holder in the retracted position and extended from the holder in the extended position. Optionally, the engagement device forms a slidable engagement between the holder and the body structure. The holder may be configured to position the body structure within the spectrophotometer wherein at least one reaction chamber is aligned with at least one detector.

Other aspects and embodiments of the present disclosure are understood with reference to the figures and following description.

BRIEF DESCRIPTION OF THE DRAWINGS

In the accompanying drawings, which form a part of the specification and are to be read in conjunction therewith, and in which like reference numerals are used to indicate like features in the various views:

FIG. 2A is a plan view in accordance with embodiments, namely of microfluidic assembly 102;

FIG. 2B is a plan view in accordance with other embodiments of a microfluidic assembly;

FIG. 4A is a perspective view of a triangular holder in a collapsed configuration with a microfluidic device in a retracted position;

FIG. 4B is a perspective view of the triangular holder of FIG. 4A in an expanded configuration with the microfluidic device of FIG. 4A in a retracted position;

FIG. 4C is a perspective view of the triangular holder of FIG. 4A in an expanded configuration with a microfluidic device in an extended position;

DETAILED DESCRIPTION OF THE DISCLOSURE

Figure 1A:
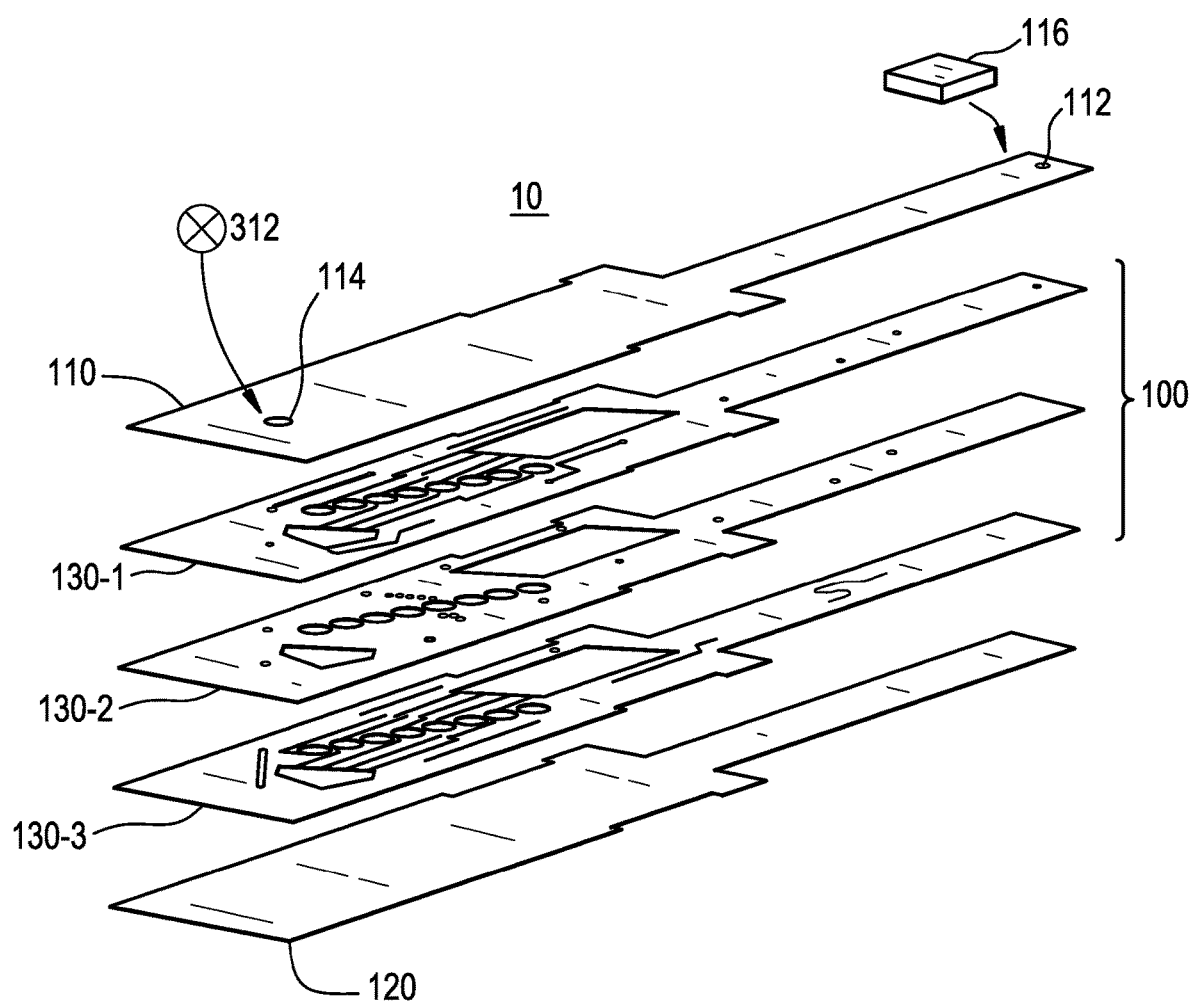
FIG. 1A is an exploded perspective view of the various layers of microfluidic device including microfluidic assembly 100 layers and features fabricated therein, in accordance with embodiments of this disclosure.

As used herein, the term "fluid" is understood broadly as any substance that continually deforms (flows) under an applied shear stress or other external force. In some examples, a fluid may include an analyte, a reagent, and/or a reactant. Biological fluids that may be used in accordance with the principles of this disclosure include, for example, urine, blood, serum, plasma, saliva, seminal fluid, sweat, lacrimal fluid (tears), and like organic fluids.

As used herein, the term "analyte" is understood as any substance within a fluid that may be placed in a microfluidic diagnostic chip (MDC) to be analyzed. Typically, the analyte is soluble or dissolved in the fluid (i.e., the biological fluid) but analytes in suspension also may be analyzed using an MDC.

Current diagnostic point-of-care devices are prone to inaccurate readings, (as discovered by the inventors of this disclosure) arising from a number of procedural and structural deficiencies and limitations. More specifically, numerous drawbacks have been discovered by the inventors of the present disclosure. First, reactions between the test sample and the test reagents on many strips begin the moment the sample and the reagents come into contact. Given that this procedure is often performed manually, the time lapse between the beginning of the reactions and the actual measurements may be arbitrary and may vary from test to test, leading to inconsistent results. Second, many test strips utilize reflectance measurements to quantify the chemical reactions taking place. While each test site is often comprised of several layers of reagents, each of which reacts with the sample, only the uppermost layer is visible. Additionally, where a smartphone camera is used to perform measurements in a non-enclosed space, reflectance testing is sensitive both to the quality of the camera and to the ambient lighting conditions of the surrounding environment, which may result in low accuracy measurements. Furthermore, where too much sample is dispensed on a test site by a non-technical individual, this can cause a meniscus to form which reflects light and thus adversely affect the interpretation of the result when using reflectance testing. Third, cross-contamination between test sites on each test strip is commonplace due to the non-isolated nature of the sites.

Numerous other problems exist to date.

As a result, this disclosure is directed to systems, devices and methods that are at least one or more of the following: automated, perform more accurate types of measurements, isolate test sites, synchronize chemical reactions with measurements taken in real time, and enable tests to be performed with a minimum of sample, which optionally is gathered in a convenient way.

This disclosure provides a microfluidic system for performing a plurality of simultaneous measurement tests on a single fluid sample across a plurality of integrated reaction chambers within a microfluidic assembly. The reaction chambers are adapted to accommodate not only reflectance-based optical testing, but also absorbance- and transmittance-based optical testing for increased sensitivity and accuracy, such as via more options to monitor chemical reactions, which provides more ways to measure the same chemistry and added ability to measure chemistries that cannot be read by reflectance. In some embodiments, such as when using paper pads, this flexibility enables more sensitive measurements. The system includes a point-of-care system with an easy-to-use applicator to collect the fluid sample and a fully automated test and measurement system to perform the tests.

The movement of the fluid within the microfluidic system (e.g., into the reaction chambers) is controlled in unison with the optical testing, allowing for the chemical reactions within each chamber to be measured as a function of time. Test conditions (e.g., the color and intensity of the source light) for each individual reaction chamber may be customized depending on the specific analytes and/or reagents within each chamber and the corresponding tests to be performed.

As described herein, channels within the microfluidic system generally include one or more of fluid passageway(s), flow path(s) and conduit(s) through which a fluid sample flows, and reaction chambers include one or more of well(s) and borehole(s) within which the fluid sample may be collected. In general, fluid sample flows through the channels to the reaction chambers where it is immobilized and tested, although in some cases measurements may be performed on a sample which is not immobilized, but is continuously flowing through the reaction chamber.

Figure 1B:
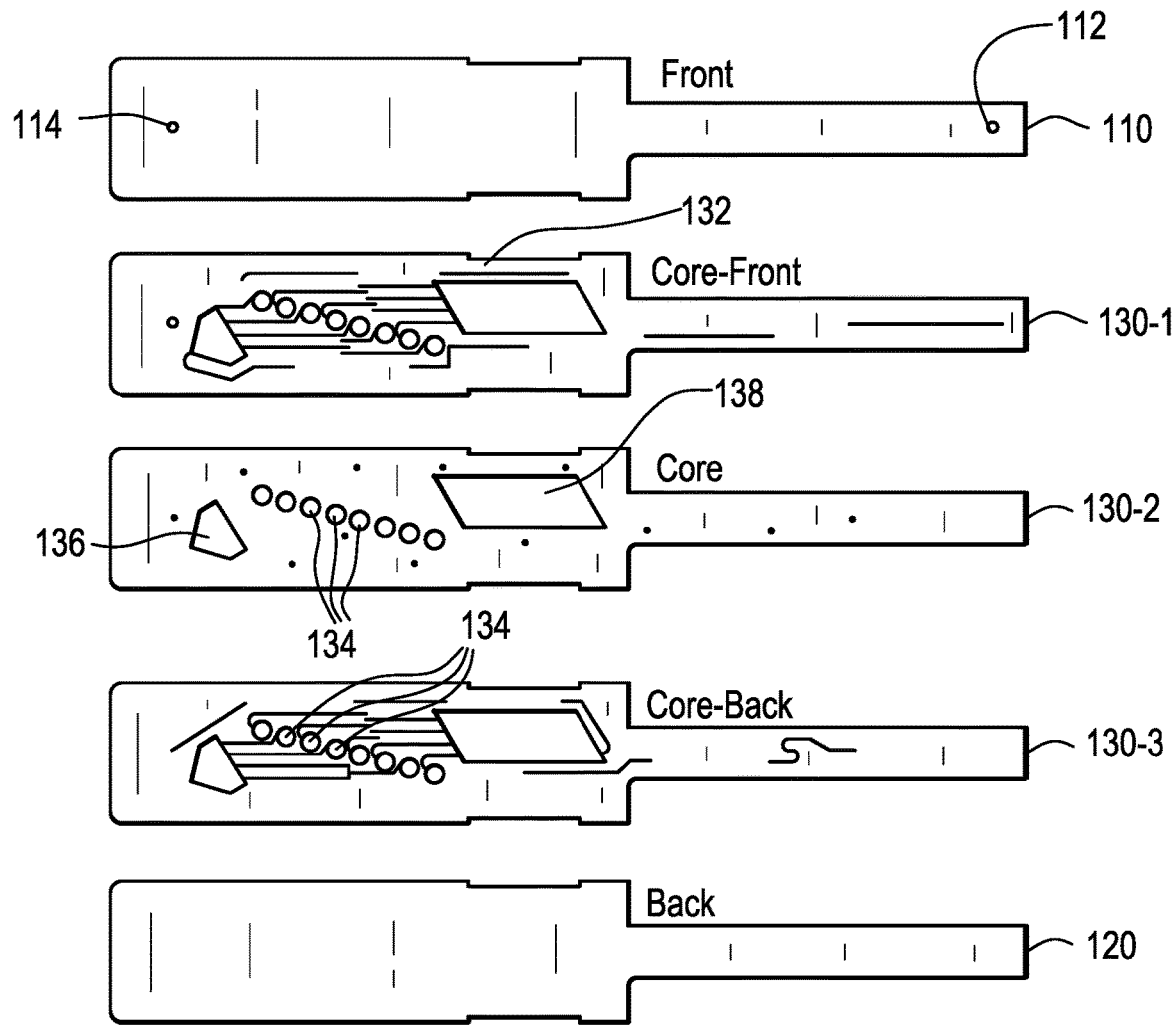
FIG. 1B is a top plan view of the various layers illustrated in FIG. 1A.
Figure 1C:
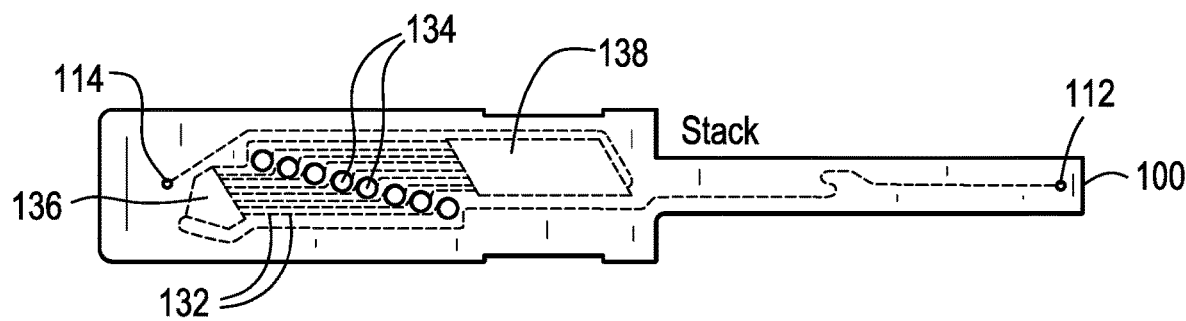
FIG. 1C is a top plan view of the layers of FIG. 1B when stacked into an assembly.

FIGS. 1A, 1B, and 1C illustrate several features of some embodiments that include one or more microfluidic device(s). For example, microfluidic device 10 is constructed according to the principles of this disclosure. Specifically, FIG. 1A shows in an exploded view of a multi-layer microfluidic device 10 which has a first outer layer 110 (e.g., a top layer) and a second outer layer 120 (e.g., a bottom layer), and one or more substrate layers 130 disposed therebetween. FIG. 1A illustrates a microfluidic device 10 having three substrate layers (i.e., layers 130-1, 130-2, and 130-3), but it is understood that any number of layers may be used (e.g., 1, 2, 3, 4, 5, 6, 7, 8, 9, 10, or more). All substrate layers 130-1 through 130-n together may be referred to as microfluidic assembly 100. FIG. 1B illustrates the various layers of the microfluidic device 10 individually, in top plan views, so that microfluidic channels, chambers, and design principles are more clearly depicted. FIG. 1C shows, in a top plan view, the assembly of the layers from FIG. 1B into a single laminate.

As seen in FIGS. 1A, 1B, microfluidic device 10 includes a first port 112 in the first outer layer 110 and a second port 114 in either the first outer layer 110 or the second outer layer 120. FIGS. 1A and 1B illustrate the second port 114 in the first outer layer 110 (i.e., the same outer layer as the first port 112), but it is understood that in alternative embodiments the second port may be conveniently located in the second outer layer 120 as the microfluidic channel design dictates. First port 112 defines the upstream end of microfluidic assembly 100 and functions as an inlet port and is adapted to accept a liquid sample from the exterior of microfluidic device 10 and direct that liquid sample into the microfluidic assembly 100. Second port 114 defines the downstream end of microfluidic assembly 100. Optionally, second port 114 is adapted to be attached to a vacuum source to facilitate liquid sample movement in a downstream direction. Thus, microfluidic assembly 100 defines a fluid flow path between the first port 112 and second port 114. Preferably, a sample fluid collection pad 116 is disposed (but need not be disposed) over and in fluid communication with first port 112, as seen in FIG. 1A. In FIGS. 1A, 1B, and 1C, microfluidic assembly 100 includes a series of microfluidic channels 132 and reaction chambers 134. Optionally, microfluidic assembly 100 further includes one or more reservoirs, such as for example, a reaction chamber manifold 136-1 and a waste reservoir 138. In embodiments, pressure reservoir 136 and reaction chamber manifold 136-1 form a centralized collection site that also allows sample fluid simultaneously to pass from manifold 136-1 towards multiple reaction chambers, whereby distinct application of a single negative vacuum force draws (or single positive pressure force pushes) sample simultaneously to (and optionally then simultaneously through), all (or at least more than one) of the reaction chambers. Such single application(s) of force may be continuous or in discrete bursts. For example, reaction chamber manifold 136-1 includes one or more sample containment outlet wall(s) 137 along it perimeter, at least one of which outlet wall(s) 137 has a plurality of side-by-side outlets 139 and each of the outlets 139 leading to a microfluidic channel 132 that takes sample to a single, sample reaction chamber. In embodiments, passages running from outlets 139 are disposed perpendicular to the multichannel gate 139-1 formed in outlet wall(s) 137 by the multiple outlets 139.

Additional functions and features of these elements are described in more detail below. FIG. 1B further illustrates that these features may span a single or a plurality of substrate layers 130, depending upon the specific element and its intended function. For example, the microfluidic channels 132 may be the width of a single substrate layer 130, but may be designed such that the fluid flow path traverses layers in a vertical direction instead of remaining on a single layer. Larger structures such as reaction chambers 134 and/or reservoirs 136, 138 may span two, three, four, five, six, or more layers in a vertical direction in order to provide the desired volume while minimizing the surface area required for that element. The various elements are fabricated into the plurality of substrate layers 130 such that the complete fluid flow path between the first port 112 and the second port 114 is formed when the substrate layers 130 are assembled/stacked.

The "substrate layers" refer to solid planar substrates having first and second opposing, or substantially parallel, planar surfaces. A variety of substrate materials may be employed as the various layers of the device. Typically, because the devices are microfabricated, substrate materials will be selected based upon their compatibility with known microfabrication techniques, e.g., photolithography, wet chemical etching, laser ablation, air abrasion techniques, injection molding, embossing, laser cutting, and other techniques. The substrate materials are also generally selected for their compatibility with the full range of conditions to which the microfluidic devices may be exposed, including extremes of pH, temperature, salt concentration, and application of electric fields. Substrates are also generally selected for their electrokinetic properties, e.g., surface potential, thermal and optical properties, e.g., transparency etc.

In some embodiments, the substrate layers 130 may be constructed from hydrophobic paper, plastic, or other nonporous and hydrophobic polymer substrate into which microfluidic channels can be formed including, for example, polymethylmethacrylate (PMMA), polycarbonate, polytetrafluoroethylene (TEFLON®), polyvinylchloride (PVC), polydimethylsiloxane (PDMS), polysulfone, and the like. In some embodiments, the first outer layer 110, the second outer layer 120, or both may include a transparent or translucent region overlying the reaction chambers 134 that are adapted such that the contents of the reaction chambers 134 may be assessed by an optical detector as described in more detail below.

The various outer layers 110, 120 and substrate layers 130 are mated, fused, or bonded together to form microfluidic assembly 100 of device 10. Mating, bonding, or fusing of the layers 110, 120, 130 is generally carried out under any of a number of methods or conditions known in the art. Conditions under which substrates may be bonded together are generally widely understood, and such bonding of substrates is generally carried out by any number of methods which may vary depending upon the nature of the substrate materials used. For example, thermal bonding of substrates may be applied to a number of substrate materials, including, e.g., glass or silica-based substrates, as well as polymer-based substrates. Such thermal bonding typically includes mating together the substrates that are to be bonded, under conditions of elevated temperature and, in some cases, application of external pressure. The precise temperatures and pressures will generally vary depending upon the nature of the substrate materials used. Generally, the temperatures required for bonding polymeric substrates will vary from about 80° C. to about 200° C., depending upon the polymeric material used. Adhesives may be used to bond substrates together according to well-known methods, which typically contemplate applying a layer of adhesive between the substrates that are to be bonded and pressing them together until the adhesive sets. A variety of adhesives may be used in accordance with these methods, including, e.g., UV curable adhesives, that are commercially available. Alternative methods may also be used to bond substrates together in accordance with the present disclosure, including. e.g., acoustic or ultrasonic welding, laser, RF welding and/or solvent welding of polymeric parts.

Optionally, as seen in FIG. 1A, an absorbent sample collection pad 116 is affixed to the outer surface of first outer layer 110 covering and in fluid communication with first port 112. Retention reservoir 116 is designed to one or more of absorb and retain a liquid sample so that the sample may be drawn through first port 112. Second port 114 is preferably connected to a vacuum source or microfluidic vacuum pump 312 such that, in operation, a vacuum or negative pressure is applied at the downstream end (second port 114) of microfluidic assembly 100 sufficient to draw or assist in drawing fluid through that assembly 100. It is contemplated that capillary action may be used to help conduct fluid through assembly 100. In some embodiments, retention reservoir 116 is adapted to hold a total volume of fluid that is in excess of the total volume of the microfluidic assembly 100, and suction applied through second port 114 draws fluid through microfluidic assembly from pad 116 via first port 112. This configuration with a larger volume of collected fluid in the retention reservoir 116 helps minimize cavitation and air pockets in the fluid flow of the sample downstream, which may otherwise disturb accurate measurements of the device 10.

FIGS. 2A and 2B illustrate respective microfluidic assemblies 102 and 103 designed in accordance with the principles of this disclosure. For convenience, microfluidic assemblies 102 and 103 are shown as a single layer in a plan view but it is understood that the assemblies 102 and 103 may be constructed from a single or multiple substrate layers 130 as described herein. These configurations are exemplary and intended to illustrate the design principles of the disclosure rather than being limiting in any way.

Each of the microfluidic assemblies 102 and 103 in FIGS. 2A and 2B has a first (inlet) port 112, a second (outlet) port 114, and a fluid flow path therebetween. Each assembly 102, 103 has a plurality of reaction chambers 134, a pressure reservoir 136 located upstream from the reaction chambers 134 (i.e., between first port 112 and reaction chambers 134) and a post-sample-analysis waste (second) reservoir 138 located downstream from the reaction chambers 134 (i.e., between reaction chambers 134 and second port 114). This arrangement means sample analysis occurs before emptying the sample(s) into a waste reservoir 138. In some embodiments, the plurality of reaction chambers 134 are plumbed in parallel between the (e.g., pressure reservoir aspect of) reaction chamber manifold 136-1 and the waste reservoir 138. Optionally, microfluidic assembly 102 (or 103) further includes e.g., one or more of: (i) at least one hydrophobic membrane, (ii) at least one semipermeable membrane and (iii) at least one semipermeable hydrophobic membrane 140 disposed between the most downstream waste reservoir 138 and the second (outlet) port 114, covering the second port 114, or both. Semi-permeable hydrophobic membrane 140 is designed to prevent liquid from escaping microfluidic assemblies 102 and 103 and from potentially contaminating the detector and/or vacuum source 312 described in more detail below, while also enabling gas or air to escape microfluidic assembly 102 (or 103) to prevent both the excess accumulation of pressure therein, and to facilitate uninterrupted suction of sample into and through microfluidic assemblies 102 and 103. In some embodiments, containing biological samples in a disposable version of microfluidic assemblies 102 and 103 and preventing instrument contamination and a potentially biohazardous condition is critical for point-of-care and other devices that are neither disposable nor can be readily decontaminated between uses.

In use, the sample liquid is drawn by capillary action, under vacuum, or both into the microfluidic assemblies 102 and 103 through the first port 112, as seen in FIGS. 2A and 2B. The sample liquid fills the pressure (first) chamber(s) 136. Substantially no sample liquid exits the pressure chamber 136 until that chamber is filled. Providing two or more pressure chambers in series promotes substantially complete filling of the most downstream pressure chamber before sample liquid flows into the reaction chambers 134. Providing one or more pressure chambers 136 in microfluidic assemblies 102 and 103 has the advantage that sample liquid exits the most downstream pressure chamber 136 into the plurality of downstream and parallel microfluidic channels 132 simultaneously. Matching the length of microfluidic channels 132 connecting the pressure chamber 136 and two or more of the reaction chambers 134, microfluidic assemblies 102 and 103 ensures that chemical and/or detection reactions in those reactions chambers 134 are initiated simultaneously by the simultaneous introduction of sample. For example, FIG. 2B provides a microfluidic assembly 103 in which four pairs of reaction chambers 134 are matched with respect to upstream microfluidic channel 132 lengths.

Pressure Reservoir(s)

Referring again to FIGS. 1-3, it is understood that all of microfluidic assembly 100 (102 and 103) may contain two, three, four, or more upstream pressure reservoirs 136. These reservoirs 136 may have any convenient volume. However, in some embodiments, each of pressure reservoir(s) 136 have a volume at least 100%, 110%, 125%, 150%, 175%, 200%, 250%, 300%, 400%, 500%, 600% or more of the total volume of all reaction chamber(s) 134 plus the volume of the microfluidic channels 132 between the pressure reservoir 136 and the waste reservoir 138. Optionally, one or more of the pressure reservoirs 136 may include an absorbent material (e.g., sponge or gel) to facilitate substantially complete filling and/or smooth sample release into the downstream microfluidic channels 132. In some embodiments, pressure reservoir(s) 136 are sized such that they are not depleted of sample liquid during complete operation of the device. These pressure reservoirs and large volume sizes thus avoid the accidental introduction of air bubbles or cavitation into the fluid flow, thus ensuring that a full amount of sample is delivered to each reaction well 134. Preferably, smooth laminar flow through assembly 100 (or e.g., 102 or 103) is achieved. As a result, much more accurate and reliable readings are possible. Precise dosing with a pipette at the sample collection site by a skilled technician is unnecessary. Embodiments of microfluidic devices may therefore be easy to use at home for a lay consumer.

Waste Reservoir(s)

It is understood that microfluidic assemblies 100, 102 and 103 may contain one, two, three, four, or more downstream or waste reservoirs 138. These reservoirs 138 may have a volume at least 100%, 110%, 125%, 150%, 175%, 200%, 250%, 300%, 400%, 500%, 600% or more of the total volume of all reaction chamber(s) 134 plus the volume of the microfluidic channels 132 upstream of the waste reservoir 138. FIG. 2A illustrates an embodiment which contains two waste (second) reservoirs 138a, 138b. In some embodiments, the total volume of waste reservoir(s) 138a, 138b combined is greater than the total volume of all reaction chambers 134, microfluidic channels 132, and pressure reservoir(s) 132 upstream from the waste reservoir(s) 138. Optionally, one or more of the waste reservoirs 138 may include an absorbent material (e.g., sponge or gel) to reduce the likelihood that sample liquid will escape the reservoir 138 in the downstream direction and contaminate the instrument. The presence of the optional waste reservoir 138 minimizes the possibility of back pressure on the fluid flow through the assembly, which may disturb the accurate and reliable reading of the sample fluid.

Reaction Chambers

In FIGS. 2A, 2B, reaction chambers 134 may have any convenient shape and/or volume and there may be any convenient number present within microfluidic assemblies 100, 102 and 103. In some embodiments, microfluidic assembly 100 contains 2, 3, 4, 5, 6, 7, 8, 9, 10, 11, 12, 14, 16, 18, 20, or any other number of reactions chambers 134. In some embodiments, reactions chambers 134 are round, oval, ovoid, spherical, cylindrical, rectangular prism, cone, or any combination thereof. In order to increase the available volume of reactions chamber 134, without increasing the surface area occupied by each reaction chamber, reaction chambers may be formed from a void fabricated into 1, 2, 3, 4, 5, or more substrate layers 130. As illustrated in FIG. 1B, for example, reaction chambers 134 are fabricated within substrate layers 130-1, 130-2, and 130-3 such that complete reaction chambers 134 are formed when microfluidic device 10 is assembled by stacking the various substrate layers 130 between the first outer layer 110 and the second outer layer 120.

In some embodiments, the reaction chambers 134 have a reagent pad 135 containing, for example, a dried film, a paper, a gel, a sponge, and compressed cellulose. Reagent pad 135 within the reaction chambers 134 may be used to control fluid flow by slowing fluid exit thereby allowing time for an optically-detectable reaction to occur, or to retain a specific quantity of fluid, thereby prolonging the residence time of a fluid and/or reaction product for detection and retarding its exit to waste reservoir 138. Sample used for a reaction does not leave a reaction chamber 134 until a measurement(s) is/are completed, which means measurement may continue during at least any one or more of the start, the development of, and the substantial completion of a reaction, which gives a full range of times at which measurements are taken along each milestone or precise point along each reaction's history, from start to equilibrium. Furthermore, reagent pad 135 may be used to immobilize reagents within reaction chambers 134 which may generally facilitate reagent loading into the microfluidic assemblies 100, 102 and 103 and/or may be used to immobilize reagents and/or optically-detectable products.

Figure 3A:
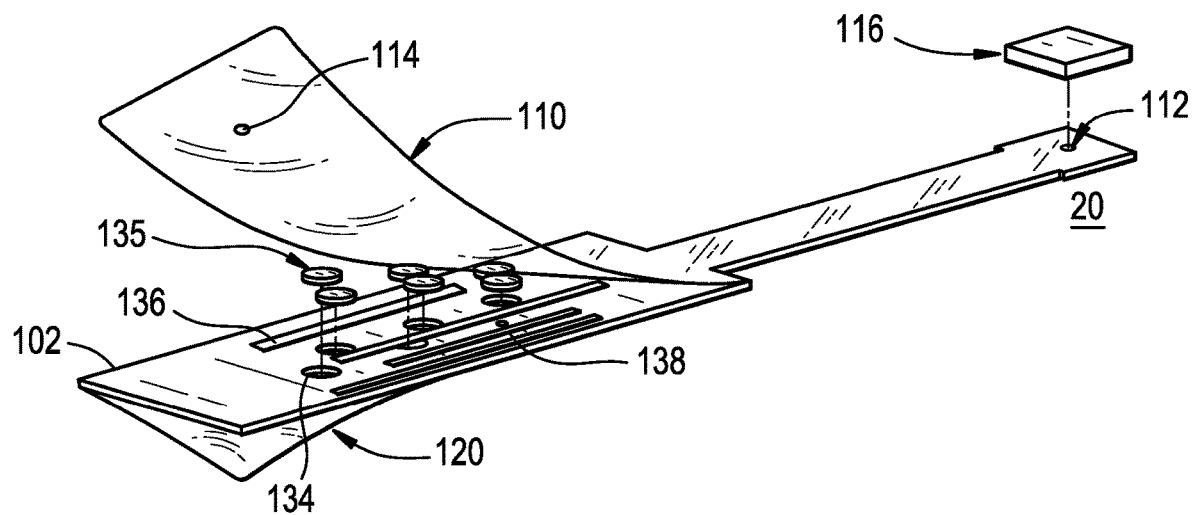
FIG. 3A is an exploded view of microfluidic device 10, according to embodiments of this disclosure.
Figure 3B:
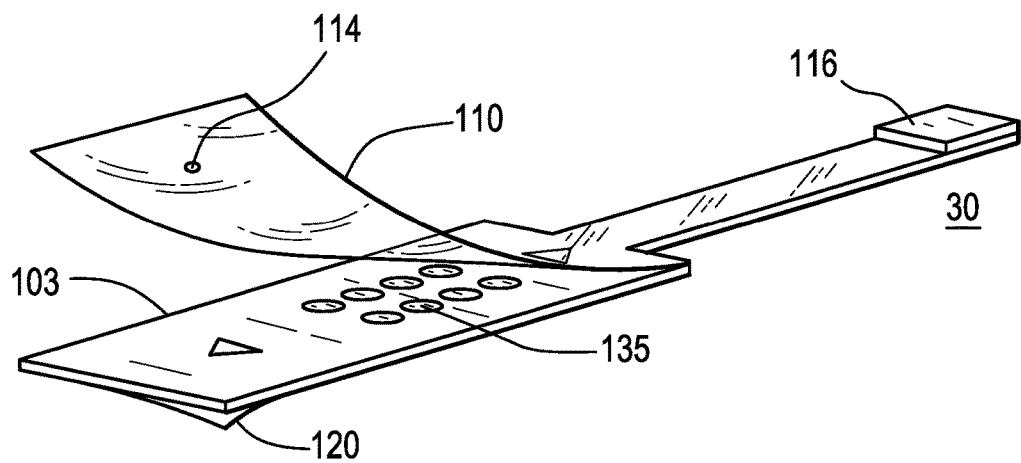
FIG. 3B is a perspective view of an assembled microfluidic device 10 according to embodiments with certain features retracted in order to illustrate internal components.

FIG. 3A provides an exploded view of microfluidic device 20 including a reagent pad 135 disposed in each reaction chamber 134. FIG. 3B shows a fully-assembled view of microfluidic device, but having first outer layer 110 and second outer layer 120 partially peeled back in order to show certain internal structures of microfluidic assembly 103. It is understood that outer layer 110 and second outer layer 120 would be adhered to microfluidic assembly 103 (or alternately, 102), not partially peeled back, when microfluidic device 30 (or 20) is fully assembled for use.

Microfluidic channels 132 (FIGS. 1B, 2A, 2B) may be described relative to reaction chambers 134 as including two distinct regions: inlet channels 132a and outlet channels 132b. Inlet channels 132a may be in fluid communication with reaction chambers 134 in any convenient configuration. For example, as illustrated in FIG. 2A, inlet channels 132a are substantially tangential to reaction chambers 134. This tangential configuration promotes swirling and reagent mixing as the fluid enters reaction chambers 134, because the fluid flow tends to circumnavigate the reaction chamber 134 perimeter. In embodiments illustrated in FIG. 2B, inlet channels 132a make a substantially radial connection with the reaction chambers 134 such that the entering fluid is directed towards the center of the reaction chamber. When used with an internal substrate or reagent pad 135 such as a sponge, compressed cellulose, paper, or the like, this configuration may promote a more consistent and even wetting and distribution of the fluid which results in more reproducible, reliable optical signals, particularly for quickly-developing reactions.

Microfluidic Device Holder

Preferred embodiments include systems, shown in FIGS. 4A-4C, 5A-5C, which also contemplate one or more holders 200 that are adapted to accept any microfluidic device (e.g., but not in any way limited to 10, 20 or 30) therein so that the use and handling of microfluidic device (e.g., 10, 20 or 30), including (urine) sample collection using retention reservoir 116, is easier and more sanitary. This is particularly advantageous for non-technical, lay individuals such as patients in a home-use setting. In some embodiments as shown here, holder 200 is foldable or collapsible to aid in packaging for shipment, housing for protection of internal structure, and aligning microfluidic device 10 with an optical detector. Further, the holder 200 and its microfluidic device may be constructed from relatively inexpensive, biodegradable materials, so both may be discarded after use.

Holder 200 generally has at least one side or end that is adapted to accept a microfluidic device. In some embodiments, a microfluidic device is retractably-engaged with holder 200 such that retention reservoir 116 may be extended from holder 200 to facilitate sample collection and retracted within holder 200 to protect against contaminating retention reservoir 116 with non-sample material before and/or after the sample is collected, and to protect against accidental contamination of the environment (e.g., the user or other person, the optical or other detection device, and/or the general surroundings) by retention reservoir 116 after sample collection (i.e., to improve sanitation). In a some embodiments, holder 200 further includes a position indicator which has a user-readable indicator to show when e.g., microfluidic device 10 is fully retracted or otherwise positioned within the holder 200 properly for detection/measurement by an optical reader adapted to accept holder 200. Microfluidic device may be contained (e.g., by being "preloaded", pre-printed, pre-fabricated, or a combination thereof) within holder 200, even if holder 200 is provided in a collapsed configuration. In this configuration, the user is required to extend microfluidic device 10 and retention reservoir 116 for sample collection and then retract microfluidic device 10 and retention reservoir 116 for assessment. Alternatively, holder 200 may be supplied separately from microfluidic device 10, requiring the user to assemble the device 10/holder 200 system prior to use.

Figure 5A:
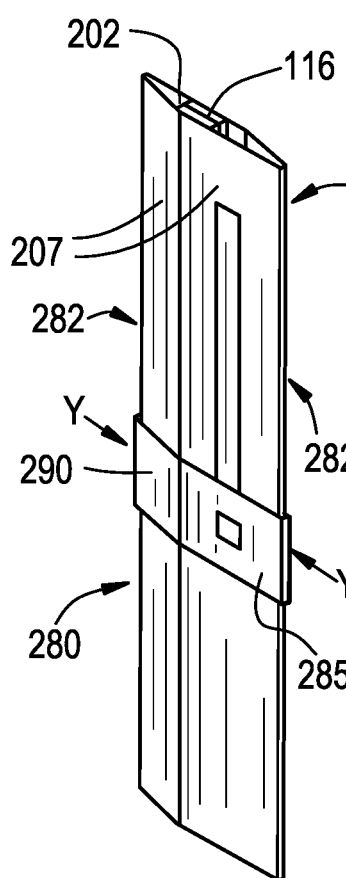
FIG. 5A is a perspective view of a rectangular holder in a collapsed configuration with a microfluidic device in a retracted position.
Figure 5B:
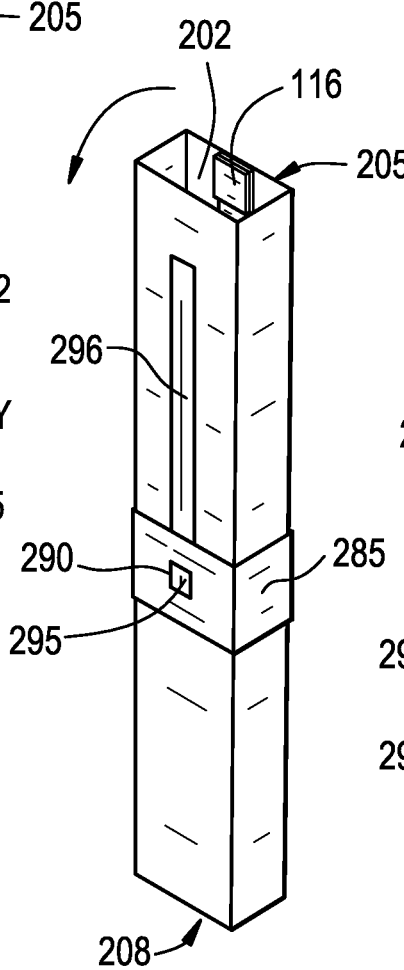
FIG. 5B is a perspective view of the rectangular holder of FIG. 5A in an expanded configuration with a microfluidic device in a retracted position.

Holder 200 either with or without microfluidic device 10 pre-loaded therein, holder 200 is provided to a user in a collapsed configuration as in FIGS. 4A, 5A. Prior to use, the user opens holder 200 into an expanded configuration. If necessary, microfluidic device 10 is loaded into expanded holder 200. Microfluidic device 10 is adjustably extendable and adjustably retractable, and is positioned in an adjustably extended configuration for sample collection (FIGS. 4C, 5C) and then retracted following sample collection for analysis (FIGS. 4B, 5B). Typically, sample analysis using microfluidic device 10 is performed with holder 200 in an expanded configuration.

Figure 5C:
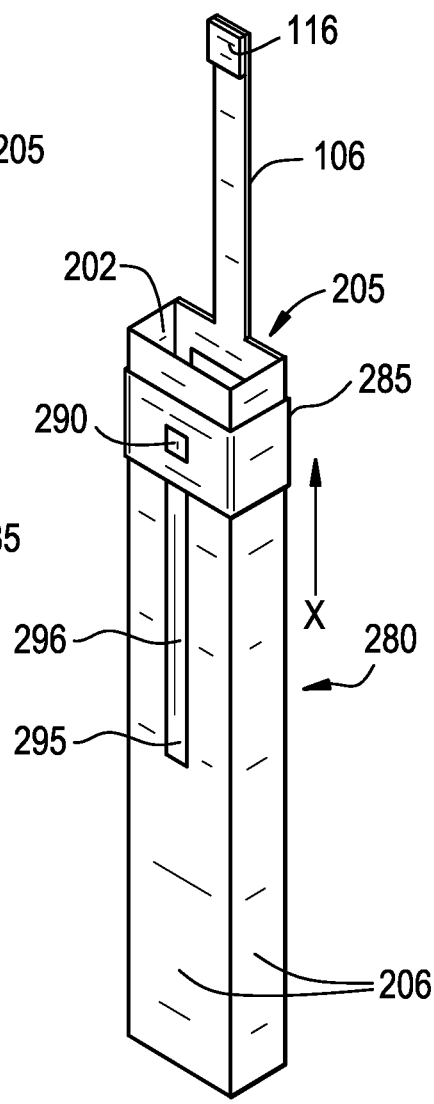
FIG. 5C is a perspective view of the rectangular holder of FIG. 5A in an expanded configuration with a microfluidic device in an extended position.

FIGS. 4A-4C illustrate features of embodiments that include a triangular-shaped and collapsible holder 200. FIGS. 5A-5C illustrate features of other embodiments that include a rectangular-shaped and collapsible holder 200. Specifically, FIGS. 4A and 5A illustrate a system in a collapsed configuration, wherein the system includes a holder 200 (or 280) and a microfluidic device 10, as described herein. In some embodiments, the system is provided to the user in the collapsed configuration to facilitate storage and handling prior to use. FIGS. 4B and 5B illustrate triangular and rectangular holders (200 and 280), respectively, in expanded configurations but with microfluidic device 10 in a fully retracted position. Arrows Y indicate the direction of force applied by the user to the holder to transition the holder from a collapsed configuration into an expanded configuration. This may be done simply by pinching the holder on edges 281 (or 282) to "pop" a holder into its three-dimensional shape having internal space 201 (or 202). FIGS. 4C and 5C illustrate the triangular and rectangular holders, respectively, in the expanded configuration and with the microfluidic device 10 in the extended position. Arrow X in FIGS. 4C, 5C indicates that, in some embodiments, position indicator 210 (or 285) is slidably engaged with the holder body and functionally attached to microfluidic device 10 such that the user may extend the microfluidic device 10 for sample collection by upwardly sliding position indicator 210 (or 285) along one or more slot(s) 217 (or 296) (or other types of openings) formed in the holder 200 (or 280). After sample collection, microfluidic device 10 may be returned to the retracted position by sliding the position indicator 210 (or 285) in the opposite direction. As discussed in more detail below, alignment window 215 (or 290) and alignment indicator 220 (or 295) may be used to indicate or confirm to the user that microfluidic device 10 is in a fully retracted position and/or appropriately positioned for alignment in the detector.

In embodiments, alignment indicators may be formed of one or more slots, but this need not be the case. For example, slots and alignment indicators may be completely separate structures and may optionally have different positions on a system from one another. Also, neither position indicators nor slots are needed where for example a position indicator slides on or along, or is part of, a framework outside of a holder (or e.g., where a holder itself comprises a mere framework.).

Holder 200 includes a plurality of sides which form an internal space 201. Specifically, holder 200 has a first end 206 and side 205 that are adapted to accept and hold microfluidic device 10 within internal space 201 and two or more sides 207 to enclose internal space 201. Holder 200 may be open at the bottom or, optionally, may have a bottom end 209 and side 203. The choice of including a bottom side 203 (not shown) and end 209 depends upon the specific configuration of the optical or other detector used to detect or measure (or both) the results from any reaction chamber(s). It is understood that these shapes are not intended to be limiting and that holders may be circular, trapezoidal, square, oval or ovoid, or any other shape that is suitable, convenient or adapted to function as described herein.

Holder 200 may optionally include a mating member that is slidably engaged with holder 200 (e.g., with first side 205). For example, a mating member may be any one or more of the following: hook(s), tab(s), knob(s), post(s), or other movable projection(s) or piece(s) having a first portion(s). Mating member is adapted to reversibly or irreversibly engage with microfluidic device 10 (via a second portion of (e.g., connected to or on) a microfluidic device that opposes the mating member(s)' first portion(s)) and the slidable engagement is adapted to move between a first extended position (FIGS. 4C, 5C) in which retention reservoir 116 and/or first port 112 is extended beyond the body of holder 200 to facilitate sample collection, and a second retracted position (FIGS. 4B, 5B) in which retention reservoir 116 and/or first port 112 is positioned within internal space 201. Optionally, the mating member is joined with position indicator 210 which is slidably engaged with holder 200 such that position indicator 210 may be translocated between a first extended position, corresponding a first extended position of the mating member, and a second retracted position corresponding to a second retracted position of the mating member.

Position indicator 210 is adapted to provide a visual signal or indication to the user when a microfluidic device is positioned within holder 200 appropriately for use with a detector. FIGS. 4A-4B and 5A-5B illustrate one possible configuration of position indicator 210. In these embodiments, position indicator 210 is a sleeve that translocates along the exterior surface of holder 200. In embodiments, holder 200 has an alignment indicator(s) 220 marked on the external surface which is viewable through alignment window 215 on the position indicator 210. Alignment indicator 220, alignment window 215, and mating member are aligned such that alignment indicator 220 is visible through alignment window 215 when mating member and microfluidic device are in a position (e.g., a fully retracted position) that the assembly is compatible and configured for use with the detector. It is understood that there are many possible configurations of an alignment indicator system that may be used in accordance with the principles of this disclosure. For example, an alignment indication system may be simply a line, a colored dot, or mark on the exterior surface of holder 200 against which the edge of position indicator 210 should be positioned. Alternatively, the body of holder 200 may contain a transparent or translucent alignment window 215 and the body of alignment indicator 220 may be contained within internal space 201 such that alignment indicator 220 is viewable through alignment window 215 when microfluidic device 10 is appropriately positioned.

Figure 6A:
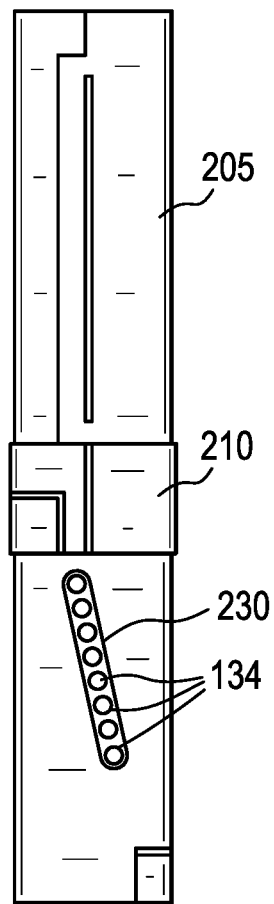
FIGS. 6A and 6B are plan views of one side of a holder illustrating configurations of the detection apertures and reaction chambers, in accordance with embodiments of this disclosure.
Figure 6B:
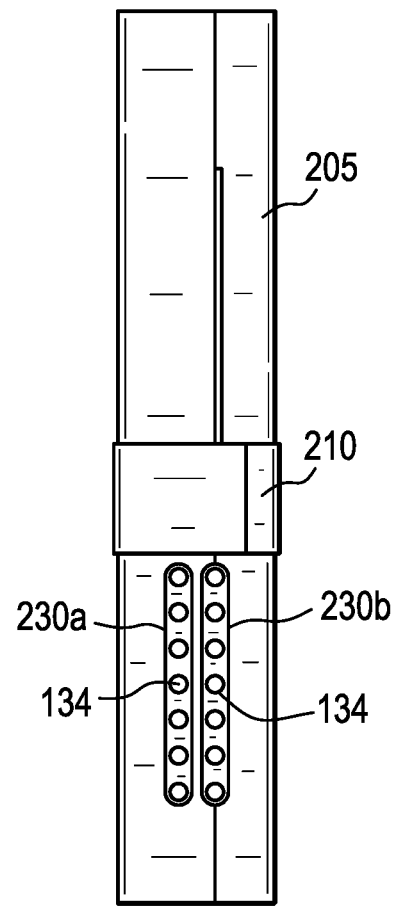

FIGS. 6A-6B provide an elevation view of first side 205 for a holder 200 and microfluidic device 10 assembly in the retracted position in which reaction chambers 134 are viewable through detection apertures 230. The illustrated configurations of reaction chambers 134 and detection apertures 230 are not intended to be limiting, but instead to illustrate the principles of the disclosure. For example, first side 205 may include a single detection aperture 230 for viewing a single or multiple reaction chambers 134, multiple detection apertures 230 each for viewing a single or multiple reaction chambers 134, or any combination thereof. In embodiments, first side 205 features a plurality of detection apertures 230, each for viewing a single reaction chamber 134.

Detection Systems

Microfluidic device 10 may be read using any suitably-configured detection system including an optical detection system or microfluidic detection chip. Such a microfluidic detection chip can be sourced from, for example, ams AG, Tobelbader Strasse 30, 8141 Premstaetten, Austria, model no. AS7262 or AS7341 spectral sensing chip, at website: https://ams.com/as7262 and https://ams.com/as7341 respectively or https://ams.com/as7262?fbclid=IwAR1TD1HQDMLqS74qKoFRKk3rC672ywxm Q1uJhe_EUC XH9zdwndT7ph2J-78.

The detection system typically includes collection optics for gathering a light-based signal transmitted through the detection window associated with the reaction chamber(s) 134, and transmitting that signal to an appropriate light detector. The light detectors may be photodiodes, avalanche photodiodes, photomultiplier tubes, diode arrays, or in some cases, imaging systems, such as charged coupled devices (CCDs) and the like. In preferred embodiments, one or more of spectrometers, spectrometric chips and photodiodes may be utilized, at least in part, as the light detectors. In the case of fluorescent reagents and products, the one or more detector(s) typically include(s) a light source which produces light at an appropriate wavelength for activating the fluorescent material, as well as optics for detecting the fluorescence through the detection window and that is produced by the contents of the reaction chamber(s) 134. The light source may be any number of light sources that-provides the appropriate wavelength, including lasers, laser diodes and LEDs. Other light sources may be required for other detection systems. For example, broad band light sources are typically used in light scattering/transmissivity detection schemes, and the like.

In some embodiments, the assembly of microfluidic device 10 and holder 200 is configured to interface with a detector such that reaction chamber(s) 134 are appropriately positioned for the detector. Optionally, the detection system comprises one detector for each reaction chamber 134. Optionally, the detection system contemplates one, two, three, four, or more illumination sources and, preferably, has one illumination source for each reaction chamber 134.

In some embodiments, the microfluidic device 10/holder 200 assembly is configured to position the reactions chamber(s) 134 appropriately in the detection system.

Figure 7A:
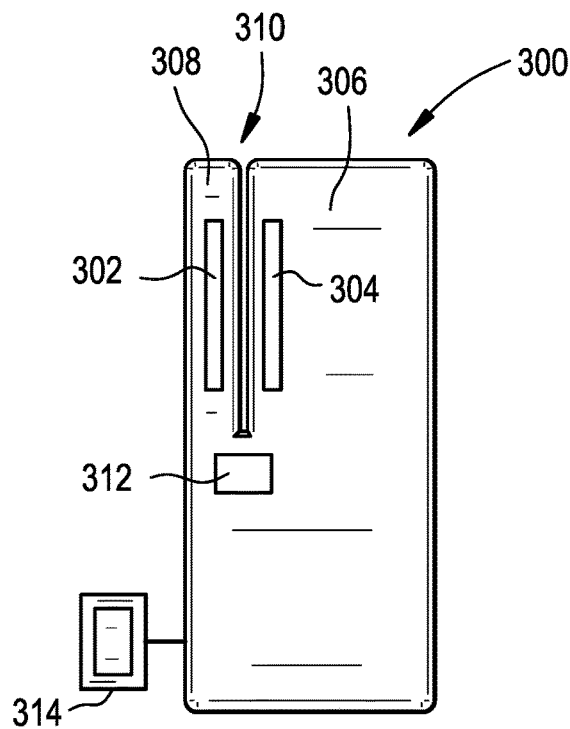
FIG. 7A is a side elevational view of an optical detection system, in accordance with embodiments.
Figure 7B:
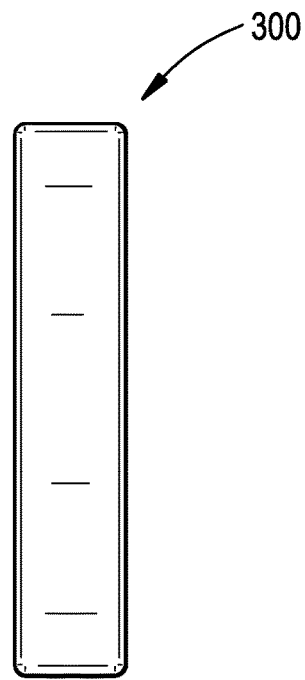
FIG. 7B is a back view of the optical detection system of FIG. 7A.
Figure 7C:
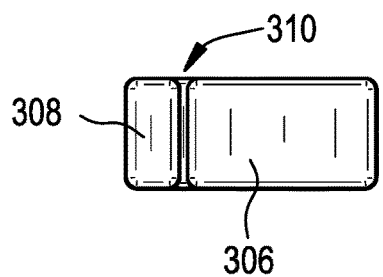
FIG. 7C is a top plan view of the optical detection system of FIG. 7A.

In embodiments shown in FIGS. 7A-7C, the system includes an optical detection system 300 having one or more light sources 302 and one or more detectors 304. The light source(s) 302 may include light emitting diodes (LEDs) or other types of sources adapted to output light at one or more desired wavelengths. Light detector(s) 304 may include solid state detectors (e.g., photodetectors) or other types of detectors adapted to detect and quantify the intensity and other characteristics of light at the wavelengths provided by source 302. In some embodiments, the optical detection system 300 includes a spectrophotometer, fluorometer, colorimeter or other type(s) of test systems. In some embodiments, the optical test and measurement system 300 performs measurements at wavelengths of 415 nm, 445 nm, 450 nm, 480 nm, 500 nm, 515 nm, 550 nm, 570 nm, 590 nm, 600 nm, 630 nm, 650 nm, 680 nm and/or 910 nm, and alternatively or additionally measures all wavelengths in the range of 350 nm to 1050 nm or other range of wavelengths, as a single optical signal integrated over the range of those wavelengths.

In embodiments, the optical detection system 300 is adapted to measure transmittance, absorbance and reflectance from or through at least one of the reaction chambers 134, thereby quantifying the analyte(s) and/or reagent(s) within each chamber 134. Prior to measurement, the optical detection system 300 may be calibrated using a reference microfluidic assembly or similar.

In embodiments, test and measurement system 300 includes main body portion 306 and upright support member 308 separated by slot 310. Upright support member 308 is adapted to support holder 200 during the optical tests of reaction chambers 134. Light sources 302 and corresponding light detectors 304 are configured on opposite sides of slot 310 such that when reaction chambers 134 are positioned within slot 310, the chambers 134 may be tested between the sources 302 and detectors 304. Light sources 302 may be configured within upright support member 308 with corresponding light detectors configured within main body portion 306 (in alignment across slot 310), or vice versa. In alternative embodiments, the light source 302 and light detectors 304 are arranged adjacent one another and on the same face of the slot 310 to measure, e.g., the reflectance of the sample within each reaction chamber 134.

Figure 8:
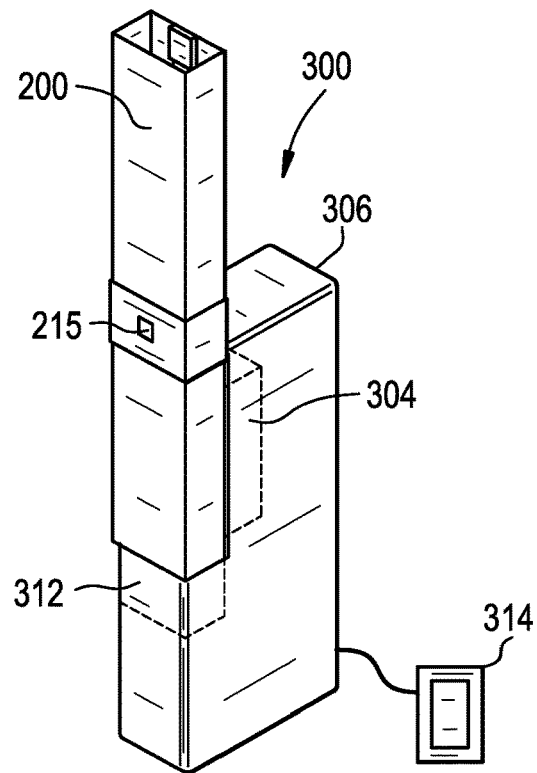
FIG. 8 is a perspective view of the optical detection system of FIG. 7 with a holder and microfluidic device in a retracted position inserted into an optical detection system for reading reaction chambers, in accordance with embodiments.

To perform a reading of a collected sample, the user places microfluidic device 10 retracted into holder 200 on upright support member 308 from above such that upright support member 308 enters the bottom end 208 and is received within inner cavity 201 of the holder. This arrangement is seen in FIG. 8, but device 10 may alternatively be inserted in similar upright (and parallel with respect to reader 300 and support member 308) fashion all by itself without holder 200 being used. The cross-section of upright support member 308 preferably matches the cross-section of holder 200 so that the upright support member 308 fits snugly within inner cavity 201. The bottom of slot 310 acts as a stop, properly positioning holder 200 onto test and measurement system 300 as shown in FIG. 8.

With holder 200 configured with upright support member 308, and with microfluidic device 10 in its retracted position, reaction chambers 134 are held within slot 310 in proper alignment with light sources 302 and light detectors 304 for optical testing. In some embodiments, each reaction chamber 134 is individually aligned with a distinct light source 302 and a corresponding detector 304 for the specific testing of the respective reaction chamber 134. Narrow slot 310 further provides an advantageous configuration, because its confined space minimizes or eliminates signal noise and interference from ambient lighting conditions, contaminants in the air or splashed fluids, accidental finger smudge, etc., that would otherwise distort the optical reading.

In some preferred embodiments, optical detection system 300 further includes a vacuum source 312 adapted to apply sufficient vacuum pressure (suction) to second port 114 to move the fluid sample from retention reservoir 116, through first port 112 and into microfluidic assembly 100, as described above. It is preferable that sufficient vacuum pressure is applied continuously until each reaction chamber 134 is filled with enough fluid sample to allow for accurate optical testing of the fluid samples within each chamber 134 by the test and measurement system 300.

In embodiments, vacuum source 312 is configured with optical detection system 300 (e.g., in main body portion 306 and/or upright support member 308) and adapted to engage second port 114 when holder 200 is mounted on upright member 308 and microfluidic device 10 is in its retracted position. Once engaged, vacuum source 312 provides adequate suction to second port 116 to move the fluid sample through microfluidic assembly 100.

In some embodiments, microfluidic system 10 includes a digital controller 314 (FIGS. 7A, 8) to simultaneously control optical detection system 300, vacuum source 312 and other elements of the system as required. Controller 314 may completely dedicated and resides on board the detection system 300, or may be connected remotely with a laptop computer, desktop computer, tablet computer, mobile device, smartphone, and/or other type of controller in communication with the system. The on-board controller 314 is integrated within the optical detection system 300 and may include digital storage retrievable by the user. Data collected by optical detection system 300 may be accessible wirelessly (e.g., Bluetooth, Wi-Fi, etc.), via hard wire via a data port, USB port, removable chip, or by other means. Alternatively, the diagnostic data may be live streamed to the user's laptop, tablet, smartphone, smartwatch, or the like.

In some embodiments, the controller 314 controls the properties of each light source 302 independently for each corresponding reaction chamber 128. For example, controller 314 may set a particular light source 302 to illuminate a particular reaction chamber 134 with a particular color and/or intensity of light specific to the analytes and/or reagents held within the respective chamber 134. In one implementation, controller 314 may set a light source 302 to white light or to a color of choice by setting the intensity of the light channels (e.g., the intensity of the red, green and blue channels of an RGB LED), respectively.

In some embodiments, the controller 314 controls vacuum source 312 and optical detection system 300 in unison, applying vacuum pressure to second port 114 to move fluid sample into each reaction chamber 134, and triggering optical detection system 300 to perform the optical tests. Optical detection system 300 may be triggered to take measurements continuously prior to the filling of the chambers 134, during the filling of the chambers 134, and after the chambers 134 are fully filled. In this way, data relating to the reactions of the analytes and/or reagents within each reaction chamber 134 are captured during the entire process in real time (without the delays or inaccuracies associated with other types of microfluidic test systems). The data then may be plotted or otherwise analyzed, for example, to determine the precise moment the reactions began within each chamber 134 and to quantify the reactions from their onset to their completion. This timing capacity is advantageous for accurate readings of the test sample, which is based on chemical reactions subject to constantly changing conditions.

"Real time" as used herein means detecting when each separate chemical reaction begins, and then tracking each (and optionally every) (or at least one of the) chemical reaction(s) from its beginning to its end, which includes and enables (i) precisely timing every time when measuring at a standard optimal point in time; and (ii) gathering of additional data on the progression of each (and optionally every) (or at least one of the) chemical reaction(s), which for such reaction chemistry develops over time rather than instantly. This real time approach enables (a) early prediction of each result before it reaches a steady-state (or equilibrium); and (b) additional ways of analyzing each light signal based on time-series data.

In addition, the wetting of any substrate within reaction chamber 134 changes its optical properties and affects the transmittance or reflectance of light. By continually monitoring the transmittance and/or absorbance properties of the substrates and reaction chambers 134 (e.g., prior, during and after the wetting of the substrate), a reaction time course may be determined.

In some embodiments, biomarker concentrations within each reaction chamber 134 are calculated using the derivative (slope) of the reaction curve, so that preliminary results may be calculated within the first few moments of the analyte and/or reagent reactions (e.g., using a first set of data taken at the onset of the reactions).

The analytes for which biomarker concentrations are observed include (but are not limited to) the following: in urine, glucose, bilirubin, beta-hydroxybutyrate (BHB), acetoacetate (AcAc), specific gravity, blood, pH, albumin protein, total protein, urobilinogen, bilirubin, nitrite, leukocytes, uristatin, creatinine, ascorbic acid (Vitamin C), biotin or its metabolites 3-hydroxyisovaleric acid or 3-methyl-crotonylglycine (Vitamin B7), folate or its metabolites para-aminobenzoylglutamate or para-acetamidobenzolygluta-mate (Vitamin B9), uric acid, urea nitrogen, sodium, potassium, magnesium, calcium, zinc, iodine, phosphorous, sulfate, oxalate, citrate, luteinizing hormone (LH), human chorionic gonadotropin (hCG), progesterone, cotinine, ethyl glucuronide (EtG), cortisol, thiobarbituric acid reactive substances (TBARS), allantoin and F2-isoprostanes, and in saliva, cortisol, glucose, pH, magnesium, calcium and phosphate.

Diaper Variation

In some alternative embodiments shown in FIGS. 9-14, the microfluidic device 10 with or without holder 200 is integrated within an item of clothing such as a diaper 400, trousers or other garment, in such a way that, preferably, (a) the retention reservoir 116 in fluid communication with the first port 112 is positioned in such a way as to enable automatic collection of a sample during the wearer's urination; (b) the parts of the microfluidic device 10 other than the retention reservoir are prevented from coming into contact with the sample by means of a sheet, film, gauze or other protective material; and (c) the microfluidic device 10 can subsequently be removed from the item of clothing by means of a release system, such as a tab, zip, wire, string, hook-and-loop fasteners, or other device, and then placed onto the optical detection system 300 for analysis.

The microfluidic device 10 may be contained within the item of clothing either by attachment to the outermost layer thereof, inserted in between the layers of material thereof, or attached to the innermost layer thereof. Modifications may be made to the relevant item of clothing to facilitate the containing of the microfluidic device 10. Where the microfluidic device is attached to the outermost layer of the item of clothing, this may include creating a partial or complete incision or aperture in the clothing material to enable the retention reservoir in communication with the first port to absorb the urine sample. Although the exemplary embodiments described below are in applications for a baby diaper, it is contemplated that the intended application may also be for adult diapers, pet diapers, and the like.

Figure 9:
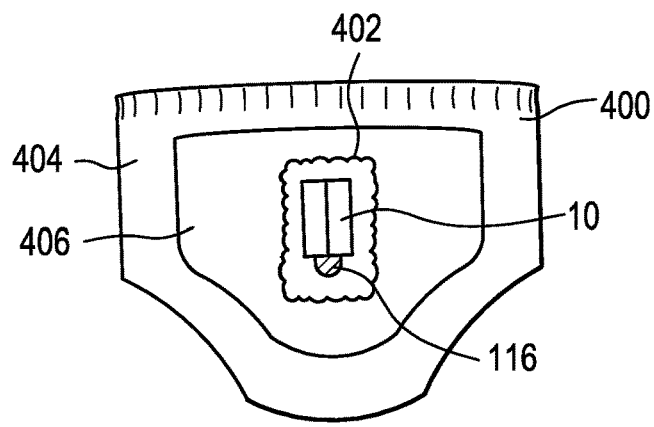
FIG. 9 is a front view of a microfluidic device according to embodiments, incorporated into an article of clothing, here a baby diaper.
Figure 10:
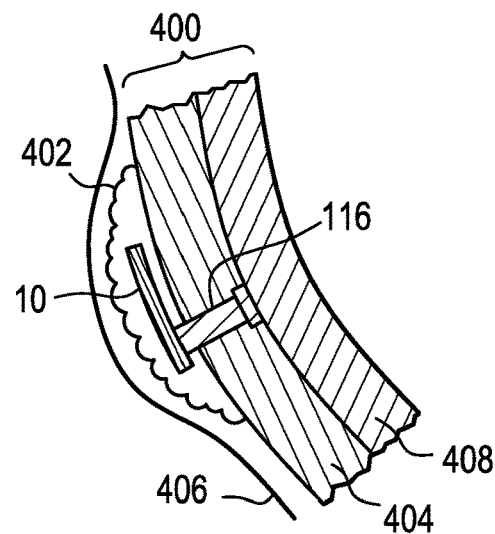
FIG. 10 is a side cross-sectional view of the diaper in FIG. 9.

FIGS. 9 and 10 show alternative embodiments of a microfluidic device 10 integrated into a baby diaper 400 for passive collection of the test sample, here, urine, through the surface of the diaper 400. The microfluidic device 10 is stitched, crimped, or held to the diaper or contained within a pocket 402 on the diaper. As seen in the cross-sectional view of FIG. 10, the retention reservoir 116 faces into the interior of the diaper and passes through the outside, liquid impermeable layer 404 of the diaper into the inner, urine wicking, permeable layer 408 that resides against the baby's body. There is an optional covering layer of fabric 406 overlying microfluidic device 10 and pocket 402, that can be liquid permeable or non-permeable, transparent or opaque. This covering layer 406 can act as a catch-all for any potential urine leaks coming from microfluidic device 10 and pocket 402.

Figure 11:
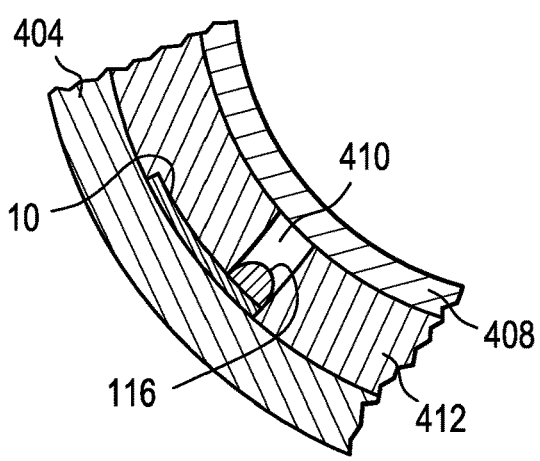
FIG. 11 is an alternative embodiment of a microfluidic device according to some embodiments integrated into a diaper from a side cross-sectional view.

FIG. 11 illustrates other alternative embodiments in a cross-sectional view having a bore hole 410 provided in a removable intermediate layer 412. The intermediate layer 412 contains the microfluidic device 10 with retention reservoir 116 disposed within bore hole 410 that is in fluid communication with permeable layer 408 of the diaper 400. The permeable layer 408 may have an aperture aligned with the bore hole 410 or the bore hole may be covered by the permeable layer. Once the urine sample is taken, the intermediate layer 412 may be detached from or slid out of the diaper 400 layers to retrieve microfluidic device 10.

Figure 12A:
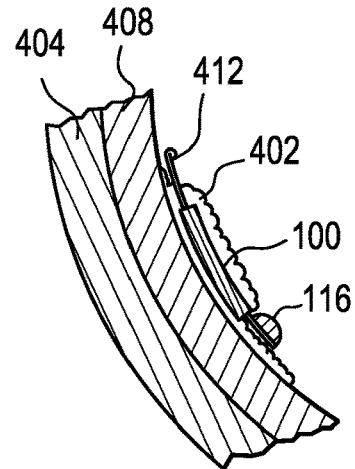
FIG. 12A illustrates a microfluidic device according to embodiments integrated into a diaper from a side cross-sectional view.
Figure 12B:
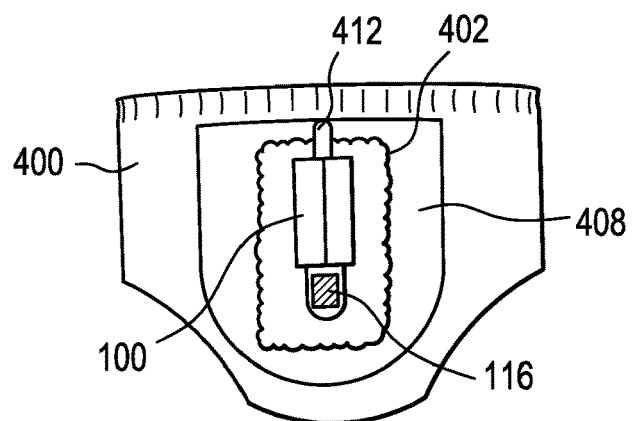
FIG. 12B is a front view of the microfluidic device and diaper shown in FIG. 12A.

FIG. 12A is a cross-sectional view and FIG. 12B is a front view of still another embodiment microfluidic device 10 disposed inside a diaper 400. The microfluidic device 10 is positioned inside the diaper overlying the urine permeable layer 408, and disposed within optional pocket 402 that is fluid impermeable to protect microfluidic device 10. Retention reservoir 116 is exposed directly to the baby's body and overlies the absorbent layer 408. A tab, string, wire or like mechanism 412 extends from microfluidic device 10, so that after the sample is collected, the parent can pull on the tab 412 to detach microfluidic device 10 from the diaper 400 for a sample reading.

Figure 13:
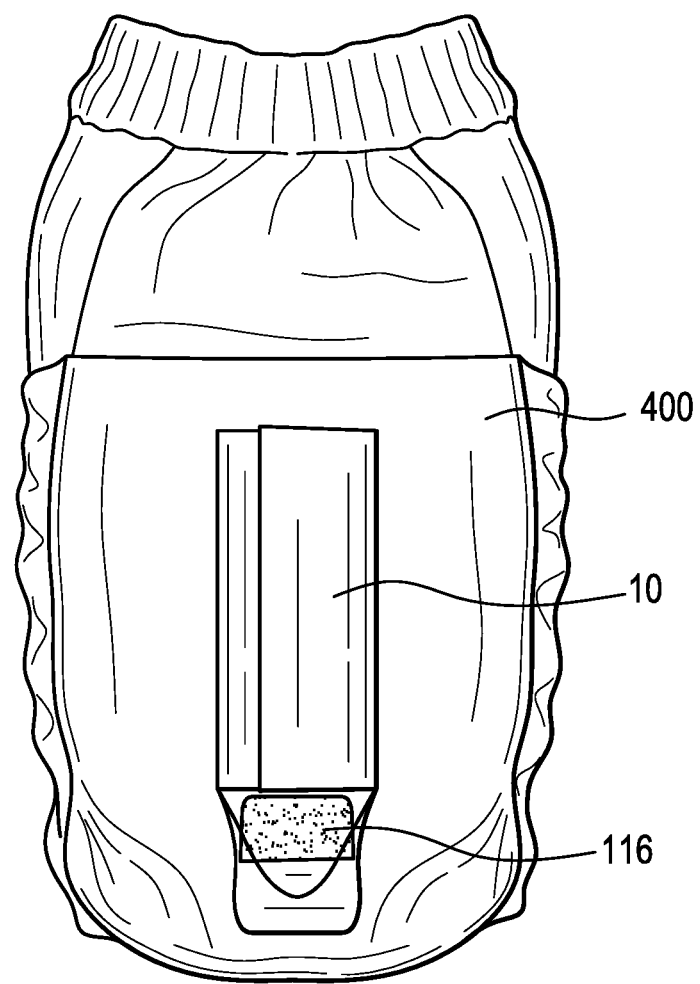
FIG. 13 is a front elevational view of a microfluidic device according to embodiments incorporated into a diaper.
Figure 14:
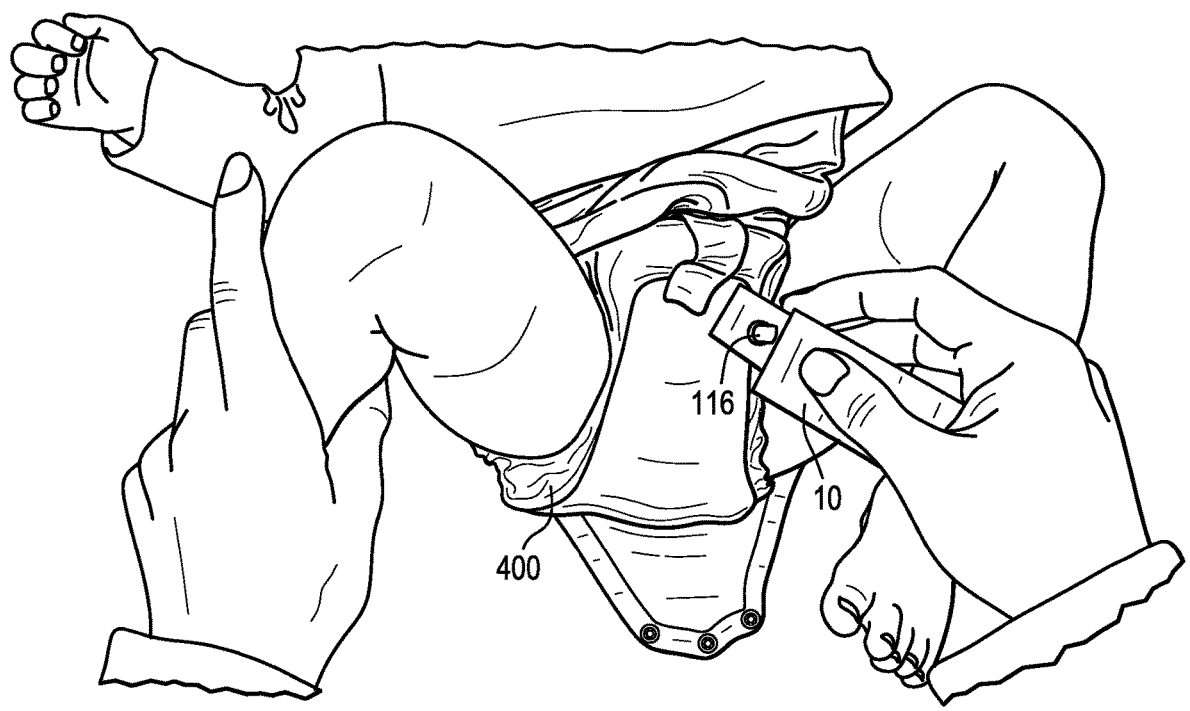
FIG. 14 is a front view of a microfluidic device according to embodiments, being retrieved from a diaper for sample analysis.

FIG. 13 is a front view illustrating other embodiments of a microfluidic device 10 integrated into a baby diaper 116. FIG. 14 shows a diaper 400 and a microfluidic device 10 with an absorbent sample pad 116 being retrieved from the diaper by the parent or caregiver.

In some embodiments, one or more microfluidic device(s) are used for toilet devices, such as when installed into a toilet. In some embodiments, e.g., the first port of microfluidic device 10 has no retention reservoir but instead is adapted to temporarily dock with a dispensing device inside a toilet that enables a sample to be drawn directly onto a microfluidic chip, either by sucking from the back outlet or bottom of microfluidic device 10, or by positive pressure pumping from the front inlet instead (i.e. using a pump in the dispensing device). The latter configuration is suitable for toilet devices because the microfluidic chip of device 10 would not be held in place, nor need to be held in place, at both its ends.

In other similar embodiments, one or more microfluidic device(s) are used as handheld testing devices, such as when at a remote location or away from an electrically powered vacuum or in a reader without a vacuum. In some embodiments, e.g., the first port of microfluidic device 10 has no retention reservoir but instead is adapted to temporarily dock with a sample dispensing device that is in fluid communication with a manual pump, such as a bister pump. These embodiments e.g., enable a sample to be drawn directly onto a microfluidic chip, either by reverse pumping action that creates a vacuum that sucks from the back outlet or bottom of a microfluidic device, or by positive pressure created by manual positive pressure pumping into the front inlet instead.

The disclosure has been described broadly and generically herein. Each of the narrower species and subgeneric groupings falling within the generic disclosure also form part of the systems, devices and methods. This includes the generic description of the systems, devices and methods with a proviso or negative limitation removing any subject matter from the genus, regardless of whether or not the excised material is specifically recited herein.

Other embodiments are within the following claims. In addition, where features or aspects of the methods are described in terms of Markush groups, those of ordinary skill in the art will recognize that the disclosure is also thereby described in terms of any individual member or subgroup of members of the Markush group.

It is understood by a person of ordinary skill in the art, upon reading this specification, that any of the aspects, elements and/or details of any of the embodiments described herein or otherwise may be combined in any way, and that the scope of the disclosure includes any combinations of any aspects, elements or details of any of the embodiments hereof. For example, the following numbered clauses set forth various but non-exhaustive embodiments of the disclosure:

1. A microfluidic system or device comprising, or method comprising use of:
a body structure comprising
   a first outer layer forming a first side of the body structure;
   1.1 A microfluidic system, device or method according to any one or more of the above or below clauses, comprising a second outer layer forming a second side of the body structure;
   1.2 A microfluidic system, device or method according to any one or more of the above or below clauses, comprising a microfluidic assembly comprising at least a first substrate layer and disposed between the first outer layer and the second outer layer;
   1.3 A microfluidic system, device or method according to any one or more of the above or below clauses, comprising a first port disposed through the first outer layer and in fluid communication with the microfluidic assembly; and
   1.4 A microfluidic system, device or method according to any one or more of the above or below clauses, comprising a second port disposed through either the first outer layer or the second outer layer and adapted to be attached to a vacuum source such that a fluid flow path is defined from the first port to the second port through the microfluidic assembly;
   1.5 A microfluidic system, device or method according to any one or more of the above or below clauses, wherein the microfluidic assembly comprises:
      (i) a reaction chamber manifold and a waste reservoir; and
   1.6 A microfluidic system, device or method according to any one or more of the above or below clauses, wherein the microfluidic assembly comprises (ii) two or more fluid flow paths between the reaction chamber manifold and the waste reservoir,
   1.7 A microfluidic system, device or method according to any one or more of the above or below clauses, wherein each fluid flow path comprises at least one reaction chamber comprising a dried film, a paper, or a gel comprising one or more colorimetric test reagents;
   1.8 A microfluidic system, device or method according to any one or more of the above or below clauses, wherein the reaction chambers are adapted for an optical measurement of absorbance or transmittance;
   1.9 A microfluidic system, device or method according to any one or more of the above or below clauses, wherein the reaction chamber manifold has a volume that is greater than the volume of a reaction chamber, or the reaction chamber manifold has a volume of at least twice the volume of a reaction chamber;
   1.91 A microfluidic system, device or method according to any one or more of the above or below clauses, wherein the waste reservoir has a volume that is greater than the volume of a reaction chamber, or the waste reservoir has a volume of at least twice the volume of a reaction chamber.
2. A microfluidic system, device or method according to any one or more of the above or below clauses, wherein the body structure further comprises a retention reservoir at the first outer layer in fluid communication with the vacuum source via the second port and adapted to accept an aqueous sample.
2.1 A microfluidic system, device or method according to any one or more of the above or below clauses, wherein the retention reservoir is at least in part at the first outer layer.
3. A microfluidic system, device or method according to any one or more of the above or below clauses, wherein the absorbent pad comprises a compressed cellulose sponge.
4. A microfluidic system, device or method according to any one or more of the above or below clauses, wherein the reaction chamber manifold further comprises an absorbent material.
5. A microfluidic system, device or method according to any one or more of the above or below clauses, wherein the waste reservoir further comprises an absorbent material.
6. A microfluidic system, device or method according to any one or more of the above or below clauses, wherein the second port further comprises a hydrophobic semipermeable membrane.
7. A microfluidic system, device or method according to any one or more of the above or below clauses, wherein the microfluidic assembly comprises microfluidic channels that have a cross-sectional dimension of 0.1-350 microns or approximately 300 to 800 microns.
8. A microfluidic system, device or method according to any one or more of the above or below clauses, comprising an optical detection system comprising a light source and a detector configured to measure absorbance by or reflectance from at least one of the reaction chambers.
9. A microfluidic system, device or method according to any one or more of the above or below clauses, wherein the optical detection system comprises a spectrophotometer or colorimeter comprising a light emitting diode (LED) source and a detector configured to measure transmittance or absorbance through at least one of the reaction chambers.
10. A microfluidic system, device or method according to any one or more of the above or below clauses, wherein the spectrophotometer comprises a plurality of LED sources and detectors configured to measure transmittance through a plurality of reaction chambers.
11. A microfluidic system, device or method according to any one or more of the above or below clauses, wherein the optical detection system comprises any one or more of (i) one or more light source, (ii) a wave guide adapted to split light emitted from the light source into a plurality of beams and direct the beams onto a plurality of reaction chambers, (iii) a wave guide adapted to merge light emitted from multiple light sources onto one or more chambers and one or more detectors, and (iv) a plurality of detectors, optionally wherein a single detector is registered to each reaction chamber.

12. A microfluidic system, device or method according to any one or more of the above or below clauses, wherein at least one detector is configured to measure transmittance or absorbance of at least one wavelength selected from the group consisting of (optionally, approximately): 300 nm, 415 nm, 445 nm, 450 nm, 480 nm, 500 nm, 515 nm, 550 nm, 570 nm, 590 nm, 600 nm, 630 nm, 650 nm, 680 nm, 700 nm, 750 nm, 800 nm, 850 nm and 910 nm, and alternatively or additionally to measure transmittance or absorbance of all wavelengths in the range of 350 nm to 1050 nm or other range of wavelengths, as a single optical signal integrated over the range of those wavelengths.

13. A microfluidic system, device or method according to any one or more of the above or below clauses, wherein the system further comprises a vacuum source adapted to apply a vacuum pressure to the second port.

14. A microfluidic system, device or method according to any one or more of the above or below clauses, wherein the system further comprises a holder having an engagement device, wherein the engagement device is configured to hold the body structure in a retracted position and an extended position, wherein the first port is housed within the holder in the retracted position and extended from the holder in the extended position.

15. A microfluidic system, device or method according to any one or more of the above or below clauses, wherein the engagement device forms a slidable engagement between the holder and the body structure.

16. A microfluidic system, device or method according to any one or more of the above or below clauses, comprising a handheld holder, the holder having a frame or a housing.

17. A microfluidic system, device or method according to any one or more of the above or below clauses, wherein the holder one or more of the following:
(i) contains an integrated sensor (such as but not limited to, a camera) that observers a chemical reaction; and
(ii) comprises a casing that receives and at least partially encloses a smartphone within the holder, in which a camera of the smartphone measures progress of at least one chemical reaction in the at least one chamber.

18. A microfluidic system, device or method according to any one or more of the above or below clauses, wherein the holder is configured to position the body structure within the spectrophotometer wherein the at least one reaction chamber is aligned with at least one detector.

19. A microfluidic system, device or method according to any one or more of the above or below clauses, comprising at least one pump in fluid communication with the first port, which pushes a sample into the device (e.g., chip) using positive pressure, optionally in fluid communication with an automated pump for a toilet, or optionally in fluid communication with a manually-activated button pump or blister-style pump for a handheld test system.

20. A microfluidic system, device or method according to any one or more of the above or below clauses, comprising inserting, or removable attachment of, the microfluidic device into clothing, optionally a diaper.

21. A microfluidic system, device or method according to any one or more of the above or below clauses, comprising any one or more of (i) extending a microfluidic device (optionally from a holder) to obtain a sample, (ii) retracting the microfluidic device (optionally into the holder) for measurement of the sample.

22. A microfluidic system, device or method according to any one or more of the above or below clauses, comprising measuring (optionally, one or more chemical reaction(s)) at the at least one reaction chamber in real time.

23. A microfluidic system, device or method according to any one or more of the above or below clauses, comprising one or more of: (i) detecting at the at least one reaction chamber, when a (or each separate) chemical reaction begins; (ii) tracking a chemical reaction from its beginning to its end, which includes one or more of (a) precisely timing a start time of a measurement (optionally at a standard optimal point in time); and (b) gathering of additional data on the progression of a chemical reaction, which for the chemical reaction in the at least one reaction chamber develops over (minutes or hours of) time rather than instantly; (iii) providing an early prediction of a reaction result before a reaction in the at least one chamber reaches a steady-state (or optionally equilibrium); (iv) analyzing a reaction using light signal(s) based on (optionally pre-determined historical) time-series data; and (v) one or more of: starting, beginning measurement of, and analyzing: a reaction or each reaction using light signal(s) at an optimal time, the optimal time(s) dependent on each reagent or each reaction based on (optionally pre-determined historical (optimally, reaction-dependent)) time data.

24. A microfluidic system, device or method according to any one or more of the above or below clauses, wherein the holder is collapsible to a flat configuration (optionally, when packaged).

25. A microfluidic system, device or method according to any one or more of the above or below clauses, wherein one or more of (i) sample flows into and (ii) reactions begin at:
multiple of the at least one chamber(s) so as to allow one or more of: testing, predictive analysis, and predictive result display.

26. A microfluidic system, device or method according to any one or more of the above or below clauses, wherein the holder has a longitudinal axis and is expandable by applying a force perpendicular to the longitudinal axis, which expansion allows the holder to one or more of: (i) receive, (ii) contain and (iii) test a reaction in:
the at least one reaction chamber.

27. A microfluidic system, device or method according to any one or more of the above or below clauses, wherein the holder has a longitudinal axis along which the at least one reaction chamber is adapted to be slidably engaged (and/or optionally, slides away from a readable position when a sample is taken and slides into the readable position for reaction measurement).

While this disclosure has been described in connection with what is presently considered to be an assortment of most practical and preferred embodiments, it is to be understood that this disclosure is not to be limited to the disclosed embodiments, but is further intended to cover various modifications and equivalent arrangements included within the spirit and scope of the appended claims.

What is claimed is:

1. A microfluidic system comprising:
a body structure comprising
   (a) a first outer layer forming a first side of the body structure;
   (b) a second outer layer forming a second side of the body structure;
   (c) a microfluidic assembly comprising at least a first substrate layer and disposed between the first outer layer and the second outer layer;
   (d) a first port disposed through the first outer layer and in fluid communication with the microfluidic assembly; and
   (e) a second port disposed through either the first outer layer or the second outer layer and adapted to be attached to a vacuum source such that a fluid flow path is defined from the first port to the second port through the microfluidic assembly;
wherein the microfluidic assembly comprises:
   (i) a reaction chamber manifold and a waste reservoir; and
   (ii) two or more parallel fluid flow paths between the reaction chamber manifold and the waste reservoir, wherein each fluid flow path comprises at least one reaction chamber comprising a dried film, a paper, or a gel comprising one or more test reagents, and wherein the at least one reaction chamber is adapted for an optical measurement;
wherein the reaction chamber manifold is on a sample supply inlet of each of the two or more fluid flow paths;
wherein the reaction chamber manifold on the sample supply inlet of each of the two or more fluid flow paths has a volume greater than the volume of the at least one reaction chamber; and
wherein the waste reservoir has a volume greater than the volume of the at least one reaction chamber.

2. The microfluidic system of claim 1, further comprising:
at least one light source that operatively emits light towards the at least one reaction chamber;
at least one light detector that operatively detects light received from the at least one reaction chamber (i) prior and (ii) after a test reagent of the least one reaction chamber is wetted by a liquid sample;
at least one digital processor; and at least one memory storing instructions that, when executed by the at least one digital processor, cause the at least one digital processor to:
   receive light signal data from the light detector that is based on the light detected by the light detector (i) prior and (ii) after a test reagent of the least one reaction chamber is wetted by a liquid sample;
   calculate a time the system will use as a time deemed to be when a chemical reaction begins in the at least one reaction chamber, based on the light signal data received from the at least one light detector; and
   derive reaction signal data based on the calculated time deemed to be when the chemical reaction begins based on light signals detected by the light detector at least (i) prior and (ii) after a test reagent of the least one reaction chamber is wetted by a liquid sample.

3. The microfluidic system of claim 1, wherein the microfluidic assembly comprises microfluidic channels having a cross-sectional dimension of about 300 microns to about 800 microns.

4. The system of claim 1, wherein the microfluidic assembly is removeably attachable to clothing.

5. The microfluidic system of claim 1, comprising a handheld holder, the handheld holder having a frame or a housing.

6. The microfluidic system of claim 5, wherein the handheld holder is collapsible to a flat configuration.

7. The microfluidic system of claim 1, wherein one or more of (i) sample flows into and (ii) reactions begin at:
multiple of the at least one chamber(s) so as to allow one or more of: testing, predictive analysis, and predictive result display.

8. The microfluidic system of claim 5, wherein the handheld holder has a longitudinal axis and is expandable by applying a force perpendicular to the longitudinal axis, which expansion allows the handheld holder to one or more of: (i) receive, (ii) contain and (iii) test a reaction in:
the at least one reaction chamber.

9. The microfluidic system of claim 5, wherein the handheld holder has a longitudinal axis along which the at least one reaction chamber is adapted to be slidably engaged and slides away from a readable position when a sample is taken and slides into the readable position for reaction measurement.

10. The microfluidic system of claim 2, wherein the instructions when executed, further cause the at least one digital processor to calculate reaction status based on data collected and thereby track the chemical reaction from the chemical reaction beginning to the chemical reaction end, which includes one or more of (a) calculating a start time of a measurement prior, during, and after wetting of the at least one of the one or more test reagents; and (b) calculating reaction status based on additional data on the progression of the chemical reaction, which for the chemical reaction in the at least one reaction chamber develops over time.

11. The microfluidic system of claim 2, wherein the instructions when executed, further cause the at least one digital processor to calculate an early prediction of a reaction result before the reaction in the at least one chamber reaches a steady-state.

12. The microfluidic system of claim 2, wherein the instructions when executed, further cause the at least one digital processor to calculate analysis of the reaction using light signal(s) based on time-series data.

13. The microfluidic system of claim 2, wherein the instructions when executed, further cause the at least one processor to, one or more of: start, begin measurement of, and calculate analysis of: the reaction using light signal(s) at an optimal time(s), the optimal time(s) dependent on each reagent or the reaction based on time data.

14. The microfluidic system of claim 1, wherein the microfluidic assembly comprises microfluidic channels that have a cross-sectional dimension of 0.1 microns to 1000 microns.

15. The microfluidic system of claim 2, wherein the instructions when executed, further cause the at least one processor to, one or more of: start, begin measurement of, and calculate analysis of: the reaction using light signal(s) at an optimal time(s), the optimal time(s) dependent on each reagent or the reaction based on time data.

16. The microfluidic system of claim 1, wherein the reaction chamber manifold further comprises an absorbent material.

17. The microfluidic system of claim 1, wherein the waste reservoir further comprises an absorbent material.

18. The microfluidic system of claim 1, wherein the microfluidic assembly comprises microfluidic channels that have a cross-sectional dimension of 0.1-350 microns.

19. The microfluidic system of claim 1, further comprising an optical detection system comprising a light source and a detector configured to measure absorbance by or reflectance from the at least one reaction chamber.

20. The microfluidic system of claim 19, wherein the optical detection system comprises a spectrophotometer or colorimeter comprising a light emitting diode (LED) source and a detector configured to measure transmittance or absorbance through the at least one reaction chamber.

21. The microfluidic system of claim 20, wherein the spectrophotometer comprises a plurality of LED sources and detectors configured to measure transmittance through the at least one reaction chamber in each of the two or more fluid flow paths.

22. The microfluidic system of claim 1, wherein the microfluidic system further comprises a vacuum source adapted to apply a vacuum pressure to the second port.

23. The microfluidic system of claim 1, wherein the microfluidic system further comprises a holder having an engagement device, wherein the engagement device is configured to hold the body structure in a retracted position and an extended position, wherein the first port is housed within the holder in the retracted position and extended from the holder in the extended position.

24. The microfluidic system of claim 23, wherein the engagement device forms a slidable engagement between the holder and the body structure.

25. The microfluidic system of claim 23, wherein the holder is configured to position the body structure within a spectrophotometer wherein at least one reaction chamber is aligned with at least one detector.

26. The microfluidic system of claim 1, wherein the optical measurement comprises measurement of one or more of:
(i) absorbance,
(ii) transmittance,
(iii) reflectance, and
(iv) fluorescence.

* * * * *